United States Patent
Inoue et al.

(10) Patent No.: US 12,110,304 B2
(45) Date of Patent: Oct. 8, 2024

(54) DIVALENT PHOSPHAZENIUM SALT AND POLYALKYLENE OXIDE COMPOSITION CONTAINING THE SAME, AS WELL AS POLYURETHANE-FORMING COMPOSITION CONTAINING THE POLYALKYLENE OXIDE COMPOSITION

(71) Applicant: TOSOH CORPORATION, Shunan (JP)

(72) Inventors: Yoshiaki Inoue, Yokkaichi (JP); Toshihide Yamamoto, Yokkaichi (JP); Katsuaki Mori, Yokkaichi (JP)

(73) Assignee: TOSOH CORPORATION, Shunan (JP)

( * ) Notice: Subject to any disclaimer, the term of this patent is extended or adjusted under 35 U.S.C. 154(b) by 1068 days.

(21) Appl. No.: 16/977,734

(22) PCT Filed: Mar. 5, 2019

(86) PCT No.: PCT/JP2019/008673
§ 371 (c)(1),
(2) Date: Sep. 2, 2020

(87) PCT Pub. No.: WO2019/172266
PCT Pub. Date: Sep. 12, 2019

(65) Prior Publication Data
US 2020/0392167 A1    Dec. 17, 2020

(30) Foreign Application Priority Data

Mar. 7, 2018 (JP) .................. 2018-041179
Mar. 7, 2018 (JP) .................. 2018-041180
(Continued)

(51) Int. Cl.
- C07F 9/24 (2006.01)
- C08K 5/5399 (2006.01)
- C08L 71/02 (2006.01)

(52) U.S. Cl.
CPC .............. *C07F 9/24* (2013.01); *C08K 5/5399* (2013.01); *C08L 71/02* (2013.01)

(58) Field of Classification Search
None
See application file for complete search history.

(56) References Cited

FOREIGN PATENT DOCUMENTS

| JP | 3497054 B2 | 2/2004 |
| JP | 4201233 B2 | 12/2008 |

(Continued)

OTHER PUBLICATIONS

Machine English translation of Maruoka et al. JP 2016102177 (Year: 2016).*
Communication dated Feb. 23, 2022 from the Indian Intellectual Property Office in Application No. 202017037175.
International Search Report for PCT/JP2019/008673 dated May 21, 2019 [PCT/ISA/210].

(Continued)

*Primary Examiner* — Sudhakar Katakam
*Assistant Examiner* — Jennifer C Sawyer
(74) *Attorney, Agent, or Firm* — Sughrue Mion, PLLC

(57) ABSTRACT

Provided are a divalent phosphazenium salt which is neutral and is excellent in thermal stability and aldehyde scavenging ability, and a method for producing the same. Also provided are a polyalkylene oxide composition having a volatile aldehyde amount reduced, having generation of odor and turbidity suppressed and being excellent in urethanization reactivity, and a method for producing such a polyalkylene oxide composition, as well as a polyurethane-forming composition containing the polyalkylene oxide composition. A divalent phosphazenium salt having a specific structure. Also, a polyalkylene oxide composition comprising a divalent phosphazenium salt having a specific structure and a (Continued)

Amount of dodecylbenzenesulfonic acid to phosphazenium salt [mol/mol]

polyalkylene oxide, a method for producing the same, and a polyurethane-forming composition containing the same.

15 Claims, 4 Drawing Sheets

(30) Foreign Application Priority Data

| Mar. 20, 2018 | (JP) | ................................. | 2018-053366 |
| Mar. 26, 2018 | (JP) | ................................. | 2018-057788 |
| Mar. 26, 2018 | (JP) | ................................. | 2018-057789 |

(56) References Cited

FOREIGN PATENT DOCUMENTS

| JP | 5716382 B2 | | 5/2015 |
| JP | 2016102177 | * | 6/2016 |
| WO | 2013/015242 A1 | | 1/2013 |
| WO | 2018/025810 A1 | | 2/2018 |

OTHER PUBLICATIONS

Written Opinion for PCT/JP2019/008673 dated May 21, 2019 [PCT/ISA/237].

* cited by examiner

Amount of dodecylbenzenesulfonic acid
to phosphazenium salt [mol/mol]

DIVALENT PHOSPHAZENIUM SALT AND POLYALKYLENE OXIDE COMPOSITION CONTAINING THE SAME, AS WELL AS POLYURETHANE-FORMING COMPOSITION CONTAINING THE POLYALKYLENE OXIDE COMPOSITION

CROSS REFERENCE TO RELATED APPLICATIONS

This application is a National Stage of International Application No. PCT/JP2019/008673 filed Mar. 5, 2019, claiming priority based on Japanese Patent Application Nos. 2018-041179 filed Mar. 7, 2018, 2018-041180 filed Mar. 7, 2018, 2018-053366 filed Mar. 20, 2018, 2018-057788 filed Mar. 26, 2018 and 2018-057789 filed Mar. 26, 2018, the entire disclosures of which are incorporated by reference herein.

TECHNICAL FIELD

The present disclosure relates to a divalent phosphazenium salt and a method for producing the same. It also relates to a polyalkylene oxide composition containing the divalent phosphazenium salt, and a method for producing the same, as well as a polyurethane-forming composition containing the polyalkylene oxide composition.

BACKGROUND ART

Monovalent phosphazenium salts are known as useful organic bases.

For example, Patent Document 1 discloses a method for producing a polyoxyalkylene oxide by conducting a polymerization reaction of an alkylene oxide using a monovalent phosphazenium salt having a specific structure represented by the formula (I).

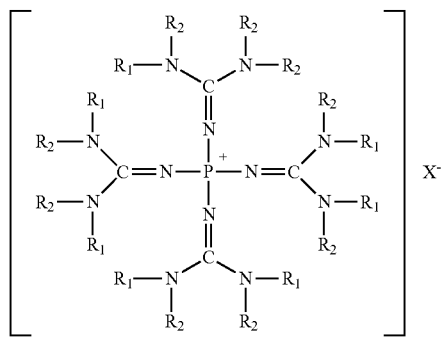

Further, Patent Document 2 discloses a method for producing a polyoxyalkylene polyol, characterized by addition-polymerizing an epoxide compound to an active hydrogen compound using a compound having a P=N bond as a catalyst, to produce a crude polyoxyalkylene polyol, and then contacting the crude polyoxyalkylene polyol and a predetermined solid acid, to control the residual amount of the catalyst in the polyoxyalkylene polyol to be at most 150 ppm. Patent Document 2 discloses a monovalent phosphazenium salt as the compound having a P=N bond.

Furthermore, a polyalkylene oxide composition containing a phosphazenium salt and a polyalkylene oxide is known.

Patent Document 1 discloses a method for producing a polyalkylene oxide by using a monovalent phosphazenium salt having a specific structure as a catalyst to produce a polyalkylene oxide, and then removing the phosphazenium salt by means of an adsorbent. The polyalkylene oxide according to Patent Document 1 is a polyalkylene oxide having a pH within a predetermined range and being excellent in urethanization reactivity.

Patent Document 2 discloses a method for producing a polyoxyalkylene polyol, characterized by addition-polymerizing an epoxide compound to an active hydrogen compound using a compound having a P=N bond as a catalyst, to produce a crude polyoxyalkylene polyol, and then contacting the crude polyoxyalkylene polyol and a predetermined solid acid, to control the residual amount of the catalyst in the polyoxyalkylene polyol to be at most 150 ppm, and the polyoxyalkylene polyol obtainable by the production method.

PRIOR ART DOCUMENTS

Patent Documents

Patent Document 1: Japanese Patent No. 5716382
Patent Document 2: Japanese Patent No. 4201233

DISCLOSURE OF INVENTION

Technical Problem

However, the monovalent phosphazenium salts according to Patent Documents 1 and 2 have been removed from the produced polyalkylene oxides because the monovalent phosphazenium salts exhibit strong basicity. Therefore, there is a need for a neutral phosphazenium salt which is not required to be removed.

By the way, a polyalkylene oxide is useful as a raw material for a resin such as polyurethane or polyester, and its applications include products to be used indoors and in vehicles. The polyalkylene oxide or a resin using the same is strongly required to reduce aldehydes to be generated in living spaces such as indoors and in vehicles.

Further, since the resin may be exposed to a high temperature in a process for producing a product in which such a resin is to be used, it is desired to be excellent in thermal stability.

Therefore, one aspect of the present invention is directed to providing a divalent phosphazenium salt which is neutral and is excellent in thermal stability and aldehyde scavenging ability, and a method for producing the same.

Further, as a result of further studies by the present inventors regarding the polyalkylene oxide according to Patent Document 1 or 2, it has been found that the polyalkylene oxide has room for further improvement in reducing the amount of volatile aldehydes. There is a strong demand for reducing aldehydes to be generated in living spaces such as indoors and in vehicles.

Further, a polyalkylene oxide is useful as a raw material for urethane or the like, and its applications include products to be used indoors and in vehicles, and therefore, suppression of generation of odor and turbidity is desired.

Therefore, one aspect of the present invention is directed to providing a polyalkylene oxide composition in which the amount of volatile aldehydes is reduced, the generation of odor and turbidity is suppressed, and the urethane-forming reactivity is excellent. Another aspect of the invention is directed to providing a method of producing such a polyalkylene oxide composition. Yet another aspect of the present invention is directed to providing a polyurethane-forming composition that contributes to formation of a polyurethane having odor and turbidity reduced.

Solution to Problem

The divalent phosphazenium salt according to one embodiment of the present invention is:
[1] a divalent phosphazenium salt represented by the formula (1):

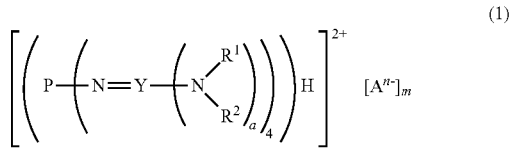

in formula (1),
$R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other;
$A^{n-}$ represents a deprotonated form of an organic sulfonic acid or organic disulfonic acid;
either one of n and m is 1, and the other is 2; and
a is 2 when Y is a carbon atom and 3 when Y is a phosphorus atom.
[2] A divalent phosphazenium salt represented by the formula (2):

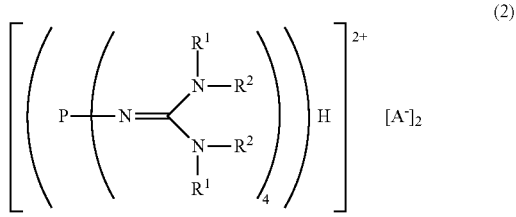

in the formula (2),
$R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and
$A^-$ represents a deprotonated form of an organic sulfonic acid.
[3] A divalent phosphazenium salt represented by the formula (3):

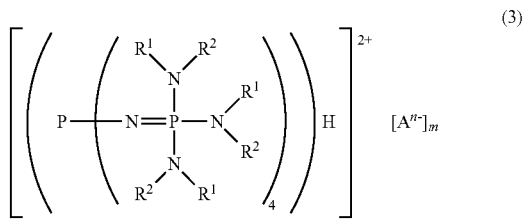

in the formula (3),
$R^1$ and $R^2$ represent each independently a hydrogen atom, a $C_{1-20}$ hydrocarbon group, a ring structure in which $R^1$ and $R^2$ are bonded to each other;

$A^{n-}$ represents a deprotonated form of an organic sulfonic acid or organic disulfonic acid; and
either one of n and m is 1 and the other is 2.
[4] The divalent phosphazenium salt according to any one of [1] to [3], characterized in that
$R^1$ and $R^2$ are methyl groups, and
$A^{n-}$ or $A^-$ is a deprotonated form of a dodecylbenzenesulfonic acid, a linear alkylbenzenesulfonic acid (soft type), or a branched chain alkylbenzenesulfonic acid (hard type).
[5] The divalent phosphazenium salt according to any one of [1] to [4], characterized in that the pH of a 0.01 mol/L aqueous solution of the divalent phosphazenium salt is at least 5 and at most 8.
[6] An aldehyde scavenger containing the divalent phosphazenium salt as defined in any one of [1] to [5].
[7] A method for producing the divalent phosphazenium salt as defined in any one of [1] to [5], characterized by reacting at least 2 mol of an organic sulfonic acid to 1 mol of the phosphazenium salt represented by the formula (4):

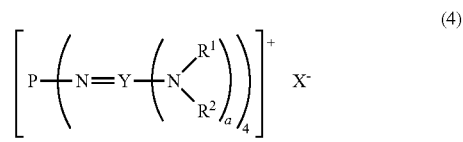

in the formula (4),
$R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other;
$X^-$ represents a hydroxy anion, a $C_{1-4}$ alkoxy anion, a carboxy anion, a $C_{2-5}$ alkylcarboxy anion, or a hydrogen carbonate anion; and
a is 2 when Y is a carbon atom and 3 when Y is a phosphorus atom.
[8] A method for producing the divalent phosphazenium salt as defined in [2], characterized by reacting at least 2 mol of an organic sulfonic acid to 1 mol of the phosphazenium salt represented by the formula (5):

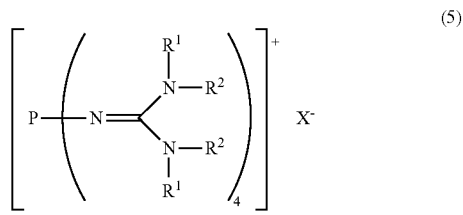

in the formula (5),
$R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and
$X^-$ represents a hydroxy anion, a $C_{1-4}$ alkoxy anion, a carboxy anion, a $C_{2-5}$ alkylcarboxy anion, or a hydrogen carbonate anion.
[9] A method for producing the divalent phosphazenium salt as defined in [3], characterized by reacting at least 2 mol of an organic sulfonic acid to 1 mol of the phosphazenium salt represented by the formula (6):

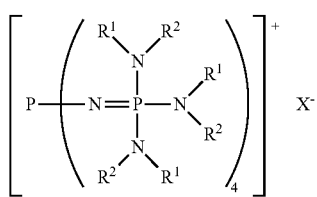

(6)

in the formula (6),

R¹ and R² represent each independently a hydrogen atom, a $C_{1-20}$ hydrocarbon group, or a ring structure in which R¹ and R² are bonded to each other;

X⁻ represents a hydroxy anion, a $C_{1-4}$ alkoxy anion, a carboxy anion, a $C_{2-5}$ alkylcarboxy anion, or a hydrogen carbonate anion.

[10] A polyalkylene oxide composition characterized by comprising the divalent phosphazenium salt as defined in any one of [1] to [5] and a polyalkylene oxide.

[11] The polyalkylene oxide composition according to [10], characterized in that when measured by the following measuring method, the amount of volatile acetaldehyde is at most 0.9 ppm, and the amount of volatile propionaldehyde is at most 3.0 ppm,

[Measurement Method]

(I): 10 g of the sample is put in a container having an internal volume of 30 ml, and (II): after (I), nitrogen bubbling is conducted at 0.5 L/min under heating at 65° C. for 2 hours to measure the amounts of volatilization.

[12] The polyalkylene oxide composition according to [10] or [11], characterized in that the pH of the polyalkylene oxide composition measured in accordance with the method described in JIS K-1557-5 is at least 5 and at most 8.

[13] A polyalkylene oxide composition characterized by comprising the divalent phosphazenium salt as defined in [2], and a polyalkylene oxide.

[14] A polyurethane-forming composition comprising (A) the polyalkylene oxide composition as defined in any one of [10] to [13], and (B) an isocyanate compound.

[15] A method for producing the polyalkylene oxide composition as defined in [13], characterized in that a polymerization reaction of an alkylene oxide is conducted in the presence of the phosphazenium salt represented by the formula (5) and an active hydrogen-containing compound to produce a polyalkylene oxide, and then, at least 2 mol of an organic sulfonic acid is added to 1 mol of the phosphazenium salt:

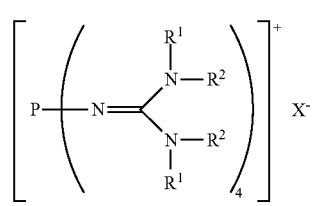

(5)

in the formula (5),

R¹ and R² represent each independently a hydrogen atom, a $C_{1-20}$ hydrocarbon group, a ring structure in which R¹ and R² are bonded to each other, or a ring structure in which a plurality of R¹ or R² are bonded to each other; and X⁻ represents a hydroxy anion, a $C_{1-4}$ alkoxy anion, a carboxy anion, a $C_{2-5}$ alkylcarboxy anion, or a hydrogen carbonate anion.

Advantageous Effects of Invention

One embodiment of the present invention can provide a divalent phosphazenium salt which is neutral and is excellent in heat stability and aldehyde scavenging ability, and a method for producing the same.

Further, one embodiment of the present invention can provide a polyalkylene oxide composition in which the amount of volatile aldehydes is reduced, and generation of odor and turbidity is suppressed, and which is excellent in the urethane-forming reactivity. Another embodiment of the present invention can provide a method for producing the polyalkylene oxide composition. Yet another embodiment of the present invention can provide a polyurethane-forming composition that contributes to formation of a polyurethane having generation of odor and turbidity suppressed.

DESCRIPTION OF EMBODIMENTS

Figure 1:
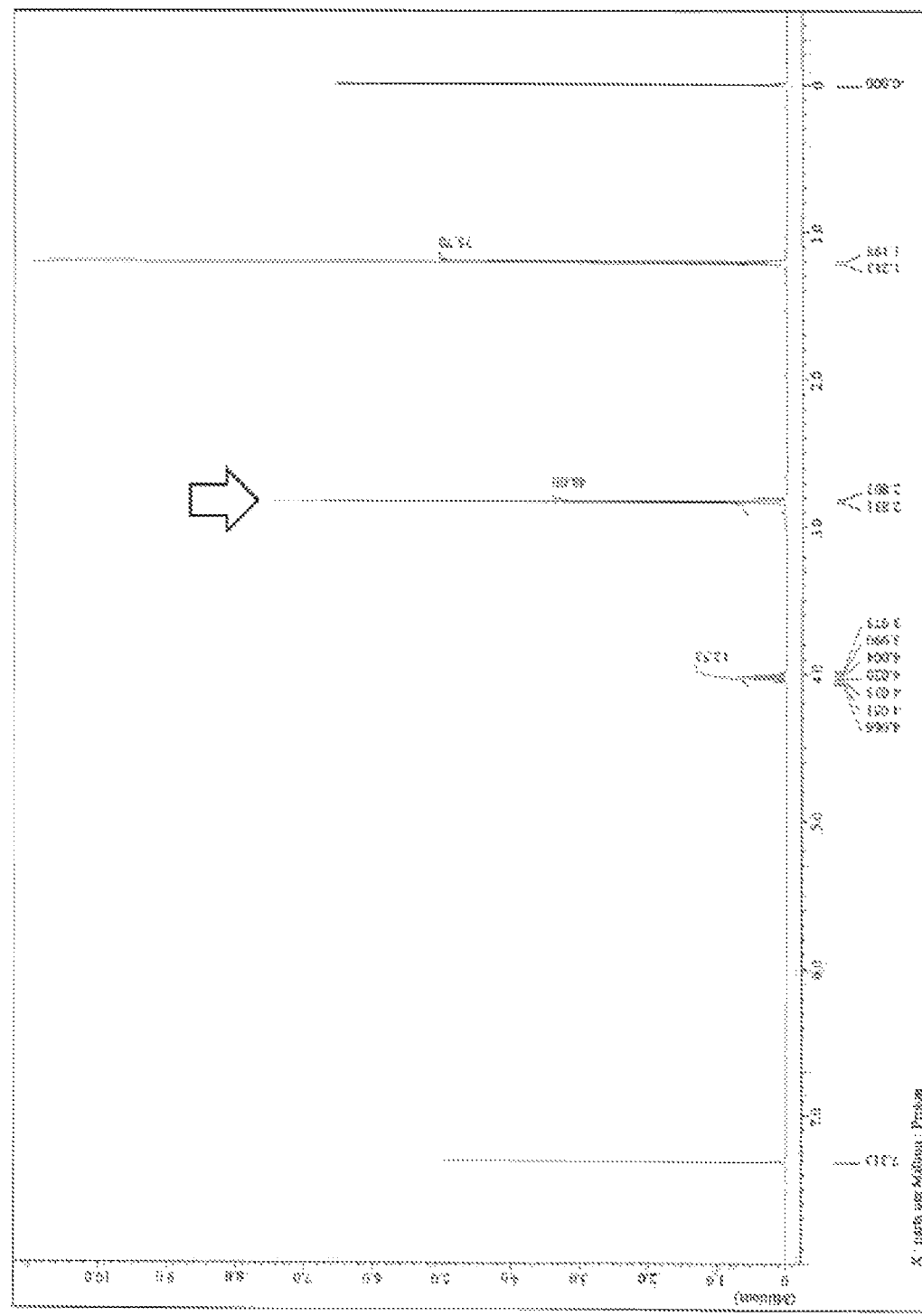
FIG. 1 is a diagram showing ¹H-NMR of a phosphazenium salt-A obtained in Synthesis Example 1.

In the following, exemplary embodiments for carrying out the present invention will be described in detail.

Divalent Phosphazenium Salts

The divalent phosphazenium salts according to one embodiment of the present invention are divalent phosphazenium salts represented by the formulae (1) to (3):

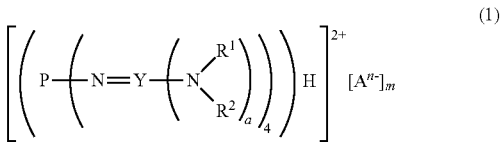

(1)

in the formula (1),

R¹ and R² represent each independently a hydrogen atom, a $C_{1-20}$ hydrocarbon group, a ring structure in which R¹ and R² are bonded to each other, or a ring structure in which a plurality of R¹ or R² are bonded to each other;

$A^{n-}$ represents a deprotonated form of an organic sulfonic acid or organic disulfonic acid;

either one of n and m is 1, and the other is 2; and a is 2 when Y is a carbon atom and 3 when Y is a phosphorus atom.

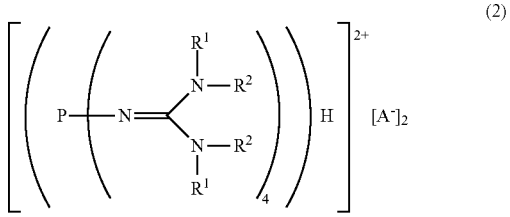

in the formula (2), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and $A^-$ represents a deprotonated form of an organic sulfonic acid.

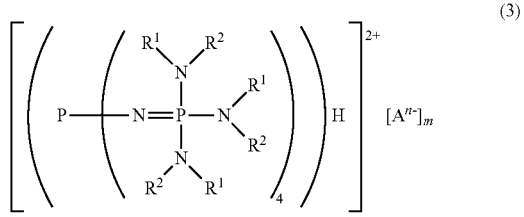

in the formula (3), $R^1$ and $R^2$ represent each independently a hydrogen atom, a $C_{1-20}$ hydrocarbon group, or a ring structure in which $R^1$ and $R^2$ are bonded to each other, $A^{n-}$ represents a deprotonated form of an organic sulfonic acid or organic disulfonic acid; and either one of n and m is 1 and the other is 2.

The divalent phosphazenium salts according to this embodiment may be any salts so long as they belong to the scopes of the salts represented by the above formulae (1) to (3).

$R^1, R^2$

In the formulae (1) to (3), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other.

The $C_{1-20}$ hydrocarbon group may, for example, be a methyl group, an ethyl group, a vinyl group, a n-propyl group, an isopropyl group, a cyclopropyl group, an allyl group, a n-butyl group, an isobutyl group, a t-butyl group, a cyclobutyl group, a n-pentyl group, a neopentyl group, a cyclopentyl group, a n-hexyl group, a cyclohexyl group, a phenyl group, a heptyl group, a cycloheptyl group, an octyl group, a cyclooctyl group, a nonyl group, a cyclononyl group, a decyl group, a cyclodecyl group, an undecyl group, a dodecyl group, a tridecyl group, a tetradecyl group, a pentadecyl group, a hexadecyl group, a heptadecyl group, an octadecyl group, a nonadecyl group, etc.

The ring structure in which $R^1$ and $R^2$ are bonded to each other, may be a pyrrolidinyl group, a pyrrolyl group, a piperidinyl group, an indolyl group, an isoindolyl group, etc.

In the formulae (1) and (2), the ring structure in which a plurality of $R^1$ or $R^2$ are bonded to each other, may, for example, be a ring structure in which two $R^1$ or two $R^2$ become each independently one group selected from alkylene groups such as a methylene group, an ethylene group, a propylene group, a butylene group, etc. and one alkylene group and the other alkylene group are bonded to each other.

Among these, from the viewpoint of easy availability of guanidines as the raw material, it is preferred that $R^1$ and $R^2$ are each independently a methyl group, an ethyl group or an isopropyl group. It is more preferred that $R^1$ and $R^2$ are methyl groups.

Specific examples of the cation species in the formulae (1) and (2) include tetrakis(1,1,3,3-tetramethylguanidino)phosphonium(hydro)dication, tetrakis(1,1,3,3-tetraethylguanidino)phosphonium(hydro)dication, tetrakis(1,1,3,3-tetra(n-propyl)guanidino)phosphonium(hydro)dication, tetrakis(1,1,3,3-tetraisopropylguanidino)phosphonium(hydro)dication, tetrakis(1,1,3,3-tetra(n-butyl)guanidino)phosphonium(hydro)dication, tetrakis(1,1,3,3-tetraphenylguanidino)phosphonium(hydro)dication, tetrakis(1,1,3,3-tetrabenzylguanidino)phosphonium(hydro)dication, tetrakis(1,3-dimethylimidazolidin-2-imino)phosphonium(hydro)dication, and tetrakis(1,3-diethylimidazolidin-2-imino)phosphonium(hydro)dication. Among them, tetrakis(1,1,3,3-tetramethylguanidino)phosphonium(hydro)dication is preferred.

Specific examples of the cation species in the formulae (1) and (3) include tetrakis[tris(dimethylamino)phosphoranylideneamino]phosphonium(hydro)dication, tetrakis[tris(diethylamino)phosphoranylideneamino]phosphonium(hydro)dication, tetrakis[tris(di-n-propylamino)phosphoranylideneamino]phosphonium(hydro)dication, tetrakis[tris(diisopropylamino)phosphoranylideneamino]phosphonium(hydro)dication, tetrakis[tris(di-n-butylamino)phosphoranylideneamino]phosphonium(hydro)dication, tetrakis[tris(diphenylamino)phosphoranylideneamino]phosphonium(hydro)dication, tetrakis[tris(dibenzylamino)phosphoranylideneamino]phosphonium(hydro)dication, tetrakis[tris(dipyrrolidinylamino)phosphoranylideneamino]phosphonium(hydro)dication, and tetrakis[tris(dipyrrolylamino)phosphoranylideneamino]phosphonium(hydro)dication. Among them, tetrakis[tris(dimethylamino)phosphoranylideneamino]phosphonium (hydro)dication is preferred.

$A^-$ and $A^{n-}$

In the formulae (1) to (3), $A^-$ represents a deprotonated form of an organic sulfonic acid. $A^{n-}$ represents a deprotonated form of an organic sulfonic acid or organic disulfonic acid. In a case where, instead of an organic sulfonic acid, an inorganic acid such as hydrochloric acid, perchloric acid, sulfuric acid, sulfurous acid or nitric acid; or an organic carboxylic acid such as acetic acid, adipic acid, benzoic acid or oxalic acid; is used, the phosphazenium salt will precipitate from inside the polyalkylene oxide, whereby the polyalkylene oxide composition becomes cloudy, and an odor derived from the acid is likely to be generated, such being undesirable.

As the organic sulfonic acid and organic disulfonic acid, any organic sulfonic acid and organic disulfonic acid may be used so long as they belong to the scopes of generally known organic sulfonic acids and organic disulfonic acids.

The organic sulfonic acid may, for example, be an alkane sulfonic acid, an α-olefin sulfonic acid, a higher alcohol sulfuric acid, a polyoxyethylene alkyl ether sulfuric acid or the like.

The organic disulfonic acid may, for example, be an alkane disulfonic acid, an α-olefin disulfonic acid, a higher alcohol disulfuric acid, a polyoxyethylene alkyl ether disulfuric acid or the like.

Specific examples of the organic sulfonic acid and organic disulfonic acid include, for example, p-toluenesulfonic acid, xylenesulfonic acid, cumenesulfonic acid, methoxybenzenesulfonic acid, dodecylbenzenesulfonic acid, a linear alkylbenzenesulfonic acid (soft type), a branched chain alkylbenzenesulfonic acid (hard type), an alkyl diphenyl ether disulfonic acid, a linear alkyl naphthalene sulfonic acid, a branched chain alkyl naphthalene sulfonic acid, a β-naphthalene sulfonic acid formalin condensate, p-aniline sulfonic acid, o-aniline sulfonic acid, etc. Among them, from the viewpoint of industrial availability and being excellent in stability of the phosphazenium salt and in aldehyde scavenging effect, dodecylbenzenesulfonic acid, a linear alkylbenzenesulfonic acid (soft type), or a branched chain alkylbenzenesulfonic acid (hard type), is preferred.

In the formulae (1) and (3), either one of n and m is 1 and the other is 2. That is, when n is 1, m is 2, and when n is 2, m is 1.

As the combination of $R^1$ and $R^2$ with $A^{n-}$ or $A^-$, from such a viewpoint that guanidines as the raw material are readily available, and being excellent in the stability of the phosphazenium salt and in aldehyde scavenging effect, it is preferred that $R^1$ and $R^2$ are methyl groups, and $A^{n-}$ or $A^-$ is a deprotonated form of dodecylbenzenesulfonic acid, a linear alkylbenzenesulfonic acid (soft type) or a branched chain alkylbenzenesulfonic acid (hard type).

The divalent phosphazenium salt according to this embodiment preferably exhibits neutrality. At the time when the divalent phosphazenium salt is added to e.g. a resin or the like, a change in pH of the resin or the like will be suppressed. The pH of a 0.01 mol/L aqueous solution of the divalent phosphazenium salt is preferably at least 5 and at most 9, more preferably at least 5 and at most 8. The pH can be measured, for example, by attaching a 0.01 mol/L aqueous solution of the divalent phosphazenium salt to a pH test paper.

The phosphazenium salt according to this embodiment is excellent in thermal stability. The divalent phosphazenium salt has no or almost no odor when subjected to heat treatment at 120° C. for 8 hours, and has no or almost no change in purity when measured by means of an NMR (nuclear magnetic resonance) apparatus.

The divalent phosphazenium salt according to this embodiment can be used as an aldehyde scavenger. For example, by adding any one of the phosphazenium salts represented by the above formulae (1) to (3) to a polyalkylene oxide, the amount of aldehyde volatilized from the polyalkylene oxide can be reduced.

Method for Producing Divalent Phosphazenium Salt

A method for producing a divalent phosphazenium salt according to one embodiment of the present invention is a method for producing a divalent phosphazenium salt represented by one of the above formulae (1) to (3), characterized by reacting at least 2 mol of an organic sulfonic acid to 1 mol of a phosphazenium salt represented by the formula (4):

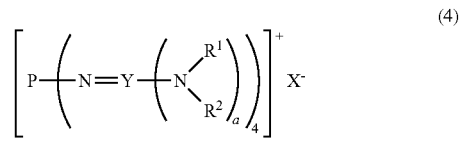

in the formula (4), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other;

$X^-$ represents a hydroxy anion, a $C_{1-4}$ alkoxy anion, a carboxy anion, a $C_{2-5}$ alkylcarboxy anion, or a hydrogen carbonate anion; and a is 2 when Y is a carbon atom and 3 when Y is a phosphorus atom.

The method for producing a divalent phosphazenium salt according to one embodiment of the present invention is the method for producing a divalent phosphazenium salt represented by the above formula (2), characterized by reacting at least 2 mol of an organic sulfonic acid to 1 mol of the phosphazenium salt represented by the formula (5):

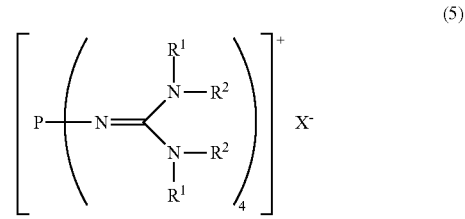

in the formula (5), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and $X^-$ represents a hydroxy anion, a $C_{1-4}$ alkoxy anion, a carboxy anion, a $C_{2-5}$ alkylcarboxy anion, or a hydrogen carbonate anion.

The method for producing a divalent phosphazenium salt according to one embodiment of the present invention is the method for producing a divalent phosphazenium salt represented by the above formula (3), characterized by reacting at least 2 mol of an organic sulfonic acid to 1 mol of the phosphazenium salt represented by the formula (6):

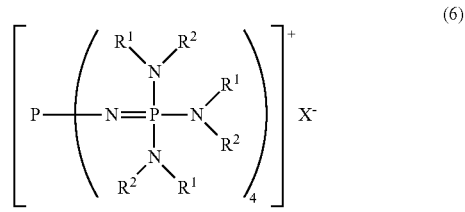

in the formula (6), $R^1$ and $R^2$ represent each independently a hydrogen atom, a $C_{1-20}$ hydrocarbon group, or a ring structure in which $R^1$ and $R^2$ are bonded to each other; and X⁻ represents a hydroxy anion, a $C_{1-4}$ alkoxy anion, a carboxy anion, a $C_{2-5}$ alkylcarboxy anion, or a hydrogen carbonate anion.

$R^1$, $R^2$

In the formulae (4) to (6), $R^1$ and $R^2$ are each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other. Specific examples thereof may be the same ones as $R^1$ and $R^2$ in the above formulae (1) to (3). And like in the above formulae (1) to (3), from the viewpoint of easy availability of the guanidines as the raw material, as $R^1$ and $R^2$, a methyl group, an ethyl group, or an isopropyl group, is preferred.

Specific examples of the monovalent phosphazenium salts represented by the formulae (4) and (5) include tetrakis(1,1,3,3-tetramethylguanidino)phosphonium hydroxide, tetrakis(1,1,3,3-tetraethylguanidino)phosphonium hydroxide, tetrakis(1,1,3,3-tetra(n-propyl)guanidino)phosphonium hydroxide, tetrakis(1,1,3,3-tetraisopropylguanidino)phosphonium hydroxide, tetrakis(1,1,3,3-tetra(n-butyl)guanidino)phosphonium hydroxide, tetrakis(1,1,3,3-tetraphenylguanidino)phosphonium hydroxide, tetrakis(1,1,3,3-tetrabenzylguanidino)phosphonium hydroxide, tetrakis(1,3-dimethylimidazolidin-2-imino)phosphonium hydroxide, tetrakis(1,3-diethylimidazolidin-2-imino)phosphonium hydroxide; tetrakis(1,1,3,3-tetramethylguanidino)phosphonium hydrogen carbonate, tetrakis(1,1,3,3-tetraethylguanidino)phosphonium hydrogen carbonate, tetrakis(1,1,3,3-tetra(n-propyl)guanidino)phosphonium hydrogen carbonate, tetrakis(1,1,3,3-tetraisopropylguanidino)phosphonium hydrogen carbonate, tetrakis(1,1,3,3-tetra(n-butyl)guanidino)phosphonium hydrogen carbonate, tetrakis(1,1,3,3-tetraphenylguanidino)phosphonium hydrogen carbonate, tetrakis(1,1,3,3-tetrabenzylguanidino)phosphonium hydrogen carbonate, tetrakis(1,3-dimethylimidazolidin-2-imino)phosphonium hydrogen carbonate, tetrakis(1,3-diethylimidazolidin-2-imino)phosphonium hydrogen carbonate, etc. Among them, from the viewpoint of the availability of guanidines as the raw material, tetrakis(1,1,3,3-tetramethylguanidino)phosphonium hydroxide is preferred.

Specific examples of the monovalent phosphazenium salts represented by the formulae (4) and (6) include tetrakis[tris(dimethylamino)phosphoranylideneamino]phosphonium hydroxide, tetrakis[tris(diethylamino)phosphoranylideneamino]phosphonium hydroxide, tetrakis[tris(di-n-propylamino)phosphoranylideneamino]phosphonium hydroxide, tetrakis[tris(diisopropylamino)phosphoranylideneamino]phosphonium hydroxide, tetrakis[tris(di-n-butylamino)phosphoranylideneamino]phosphonium hydroxide, tetrakis[tris(diphenylamino)phosphoranylideneamino]phosphonium hydroxide, tetrakis[tris(dibenzylamino)phosphoranylideneamino]phosphonium hydroxide, tetrakis[tris(dipyrrolidinylamino)phosphoranylideneamino]phosphonium hydroxide, tetrakis[tris(dipyrrolylamino)phosphoranylideneamino]phosphonium hydroxide; tetrakis[tris(dimethylamino)phosphoranylideneamino]phosphonium hydrogen carbonate, tetrakis[tris(diethylamino)phosphoranylideneamino]phosphonium hydrogen carbonate, tetrakis[tris(di-n-propylamino)phosphoranylideneamino]phosphonium hydrogen carbonate, tetrakis[tris(diisopropylamino)phosphoranylideneamino]phosphonium hydrogen carbonate, tetrakis[tris(di-n-butylamino)phosphoranylideneamino]phosphonium hydrogen carbonate, tetrakis[tris(diphenylamino)phosphoranylideneamino]phosphonium hydrogen carbonate, tetrakis[tris(dibenzylamino)phosphoranylideneamino]phosphonium hydrogen carbonate, tetrakis[tris(dipyrrolidinylamino)phosphoranylideneamino]phosphonium hydrogen carbonate, tetrakis[tris(dipyrrolylamino)phosphoranylideneamino]phosphonium hydrogen carbonate; etc. Among them, from the viewpoint of easy availability of raw materials, tetrakis[tris(dimethylamino)phosphoranylideneamino]phosphonium hydroxide and tetrakis[tris(dimethylamino)phosphoranylideneamino]phosphonium hydrogen carbonate are preferred.

The amount of the organic sulfonic acid to 1 mol of the monovalent phosphazenium salt represented by one of the formulae (4) to (6) is at least 2 mol, preferably at least 2.1 mol and at most 10 mol, more preferably at least 2.2 mol and at most 5 mol. If the amount of the organic sulfonic acid is less than 2 mol to 1 mol of the monovalent phosphazenium salt, the obtainable phosphazenium salt will be unstable, and the purity may decrease, such being undesirable.

The reaction between the monovalent phosphazenium salt represented by one of the formulae (4) to (6) and the organic sulfonic acid may be carried out in a solvent. As the solvent, water; an alcohol such as methanol, ethanol, n-propanol, isopropanol, n-butanol, isobutanol, t-butanol, n-pentanol, neopentanol, n-hexanol, n-heptanol, n-octanol, n-nonanol or n-decanol; a polyhydric alcohol such as diethylene glycol, triethylene glycol, propylene glycol, 1,3-butanediol, 1,4-butanediol, 2,3-butanediol or glycerin; a polyhydric alcohol derivative such as ethylene glycol monomethyl ether, ethylene glycol monoethyl ether, ethylene glycol monobenzyl ether or ethylene glycol monophenyl ether; a fatty acid such as formic acid or acetic acid; or a nitrogen-containing compound such as ethylenediamine, aniline or acetonitrile, may be mentioned. As the solvent, one type may be used alone, or a mixed solvent of two or more types may be used.

The phosphazenium salt according to one embodiment of the present invention is neutral and excellent in thermal stability, and further has an aldehyde scavenging effect. Therefore, at the time when the divalent phosphazenium salt is added to, for example, a polyalkylene oxide, it is possible to capture an aldehyde in the polyalkylene oxide while keeping the polyalkylene oxide neutral.

Polyalkylene Oxide Composition

A polyalkylene oxide composition according to one embodiment of the present invention contains the divalent phosphazenium salt represented by one of the above formulae (1) to (3) and a polyalkylene oxide.

Polyalkylene Oxide

As the polyalkylene oxide, any polyalkylene oxide may be used so long as it belongs to the scope generally known as a polyalkylene oxide. For example, polyethylene oxide, polypropylene oxide, poly(1,2-butylene oxide), poly(2,3-butylene oxide), polyisobutylene oxide, polybutadiene oxide, polypentene oxide, polycyclohexene oxide, polystyrene oxide, etc. may be mentioned. Further, a block copolymer and a random copolymer containing these as copolymerization components may be mentioned. Among these, polyethylene oxide, polypropylene oxide, and a polypropylene oxide-polyethylene oxide block copolymer are preferred.

In the polyalkylene oxide composition, the content of the divalent phosphazenium salt is not particularly limited, but since it is possible to obtain a polyalkylene oxide composition in which odor and turbidity are suppressed and the amount of volatile aldehyde is small, it is preferably at least 50 ppm and at most 10,000 ppm, more preferably at least 100 ppm and at most 5,000 ppm, further preferably at least 200 ppm and at most 3,000 ppm.

The polyalkylene oxide composition may contain an antioxidant. The antioxidant may, for example, be a phenolic antioxidant such as 2,6-di-tert-butyl-4-methylphenol, 2-tert-butyl-4-methoxyphenol, 2,6-di-tert-butylphenol, 6-tert-butyl-2,4-methylphenol, pentaerythritol tetrakis[3-(3,5-di-tert-butyl-4-hydroxyphenylpropionate] (e.g. Irganox 1010 manufactured by BASF), 3,5-bis-tert-butyl-4-hydroxybenzenepropanoic acid octadecyl ester (e.g. Irganox 1076 manufactured by BASF) or 3,5-bis-tert-butyl-4-hydroxybenzenepropanoic acid isooctyl ester (e.g. Irganox 1135 manufactured by BASF); or an amine-type antioxidant such as n-butyl-p-aminophenol, 4,4-dimethyldiamine or 4,4-dioctyldiphenylamine. These antioxidants may be used alone or in combination of two or more.

The polyalkylene oxide composition according to this embodiment is one having generation of odor suppressed. The polyalkylene oxide composition is one which has no odor or substantially no odor at the time when 10 g of the polyalkylene oxide composition is put in a 20 ml sample tube, left to stand still for 12 hours in the sealed state and then opened.

The polyalkylene oxide composition according to this embodiment is one having occurrence of turbidity suppressed. The polyalkylene oxide composition is one which has no turbidity or substantially no turbidity at the time when 10 g of the polyalkylene oxide composition is put in a 20 ml sample tube and visually observed.

The polyalkylene oxide composition according to this embodiment is excellent in urethanization reactivity. The polyalkylene oxide composition is preferably one, of which the pH as measured in accordance with the method described in JIS K-1557-5 is at least 5 and at most 8. When the pH is at least 5 and at most 8, the reactivity at the time when the polyalkylene oxide composition and the isocyanate compound are mixed to synthesize a polyurethane-forming composition, will be further improved, such being preferred.

The polyalkylene oxide composition according to this embodiment has little volatile aldehydes. As the index in the present embodiment, the amount of acetaldehyde to be volatilized by nitrogen bubbling (flow rate: 0.5 L/min) under heating at constant conditions (65° C., 2 hours) is preferably at most 0.9 ppm, more preferably at most 0.8 ppm. Further, the amount of propionaldehyde to be volatilized under the above conditions is preferably at most 3.0 ppm, more preferably at most 2.5 ppm.

The polyalkylene oxide composition according to this embodiment has little volatile aldehydes. As the index in the present embodiment, when measured by the following measurement method, the amount of volatile acetaldehyde is preferably at most 0.9 ppm, and the amount of volatile propionaldehyde is preferably at most 3.0 ppm:

[Measurement Method]

(I): 10 g of the sample is put in a container having an internal volume of 30 ml, and (II): after (I), nitrogen bubbling is conducted at 0.5 L/min under heating at 65° C. for 2 hours to measure the amounts of volatilization.

More specifically, when measured in the order of the following (i) to (iv), the amount of volatile acetaldehyde is preferably at most 0.9 ppm, more preferably at most 0.8 ppm. Further, when measured in the order of the following (i) to (iv), the amount of volatile propionaldehyde is preferably at most 3.0 ppm, more preferably at most 2.5 ppm.

(i) The polyalkylene oxide composition is put in an impinger having an internal capacity of 30 ml, and under heating at constant conditions (65° C., 2 hours), subjected to bubbling at 65° C. with nitrogen through a hydrocarbon trap (flow rate: 0.5 L/min), (ii) the volatilized gas is collected in a 2,4-dinitrophenyl-hydrazine (DNPH) cartridge, (iii) using 5 ml of an eluent, the adsorbed component is eluted, and (iv) high speed liquid chromatography (high performance liquid chromatography) measurement is carried out.

Method for Producing Polyalkylene Oxide Composition

As a method for producing a polyalkylene oxide composition containing the phosphazenium salt represented by the formula (1) or (3) and a polyalkylene oxide, any method may be used so long as it is a method which can produce a polyalkylene oxide composition containing the divalent phosphazenium salt represented by the above formula (1) or (3) and a polyalkylene oxide. For example, a method of mixing the divalent phosphazenium salt represented by the above formula (1) or (3) with a polyalkylene oxide may be mentioned. The temperature at which the phosphazenium salt is mixed with the polyalkylene oxide may be any temperature, and, for example, a range of from 40 to 130° C. may be mentioned.

As a method for producing a polyalkylene oxide composition containing a divalent phosphazenium salt represented by the formula (2) and a polyalkylene oxide, any method may be used so long as it is a method which can produce a polyalkylene oxide composition containing the divalent phosphazenium salt represented by the above formula (2) and a polyalkylene oxide. For example, a method of mixing the divalent phosphazenium salt represented by the above formula (2) with a polyalkylene oxide may be mentioned. Further, a method may be mentioned in which in the presence of the monovalent phosphazenium salt represented by the above formula (5) and an active hydrogen-containing compound, ring-opening polymerization of an alkylene oxide is carried out to produce a polyalkylene oxide, and then, at least 2 mol of an organic sulfonic acid is added to 1 mol of the phosphazenium salt.

A method for producing a polyalkylene oxide composition according to one embodiment of the present invention is the above method for producing a polyalkylene oxide composition, in which in the presence of the phosphazenium salt represented by the formula (5) and an active hydrogen-containing compound, a polymerization reaction of an alkylene oxide is carried out to produce a polyalkylene oxide, and then, at least 2 mol of an organic sulfonic acid is added to 1 mol of the phosphazenium salt:

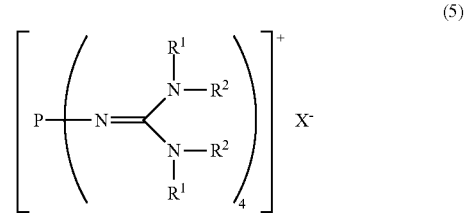

(5)

in the formula (5), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and $X^-$ represents a hydroxy anion, a $C_{1-4}$ alkoxy anion, a carboxy anion, a $C_{2-5}$ alkylcarboxy anion, or a hydrogen carbonate anion.

The alkylene oxide may, for example, be a $C_{2-20}$ alkylene oxide. Specifically, ethylene oxide, propylene oxide, 1,2-butylene oxide, 2,3-butylene oxide, isobutylene oxide, butadiene monooxide, pentene oxide, styrene oxide, cyclohexene oxide, etc. may be mentioned. Among them, ethylene oxide or propylene oxide is preferred because the alkylene oxide is easily available and the obtained polyalkylene oxide has high industrial value. As the alkylene oxide, one type may be used alone, or two or more types may be used in combination. When two or more types are used as mixed, for example, the first alkylene oxide may be reacted and then the second alkylene oxide may be reacted, or two or more types of alkylene oxide may be simultaneously reacted.

The active hydrogen-containing compound may be a hydroxy compound, an amine compound, a carboxylic acid compound, a thiol compound, a polyether polyol having a hydroxy group, etc.

The hydroxy compound may, for example, be water, ethylene glycol, diethylene glycol, propylene glycol, dipropylene glycol, 1,3-propanediol, 1,3-butanediol, 1,4-butanediol, 1,6-hexanediol, glycerin, trimethylolpropane, hexanetriol, pentaerythritol, diglycerin, sorbitol, sucrose, glucose, 2-naphthol, bisphenol, etc.

The amine compound may, for example, be ethylenediamine, N,N'-dimethylethylenediamine, piperidine, piperazine, etc.

The carboxylic acid compound may, for example, be benzoic acid, adipic acid, etc.

The thiol compound may, for example, be ethanedithiol, butanedithiol, etc.

The polyether polyol having a hydroxy group may, for example, be a polyether polyol having a hydroxy group, such as a polyether polyol having a molecular weight of from 200 to 3,000.

These active hydrogen-containing compounds may be used alone or in combination of a few types as mixed.

As the organic sulfonic acid, the same one as the organic sulfonic acid mentioned in the above formula (2) may be mentioned.

In a case where, in place of the organic sulfonic acid, an inorganic acid such as hydrochloric acid, perchloric acid, sulfuric acid, sulfurous acid or nitric acid; or an organic carboxylic acid such as acetic acid, adipic acid, benzoic acid or oxalic acid, is used, the phosphazenium salt will precipitate from inside of the polyalkylene oxide composition, whereby the polyalkylene oxide composition becomes cloudy, and an odor derived from an acid is likely to be generated, such being undesirable.

The amount of the organic sulfonic acid to be added is at least 2 mol, preferably at least 2 mol and at most 10 mol, more preferably at least 2.1 mol and at most 8 mol, further preferably at least 2.2 mol and at most 5.0 mol, to 1 mol of the phosphazenium salt represented by the above formula (5). If it is less than 2 mol, an unreacted monovalent phosphazenium salt will remain, and an odor will be generated in the polyalkylene oxide composition, such being undesirable. On the other hand, when the amount is at most 10 mol, the polyalkylene oxide composition will exhibit good liquidity (pH) and will be excellent in urethanization reactivity, such being preferred.

Polyurethane-Forming Composition

A polyurethane-forming composition according to one embodiment of the present invention comprises:

(A) a polyalkylene oxide composition containing the divalent phosphazenium salt represented by one of the above formulae (1) to (3) and a polyalkylene oxide, and (B) an isocyanate compound.

The isocyanate compound (B) may be any one so long as it is one belonging to the scope generally known as an isocyanate compound, and, for example, an aromatic isocyanate compound, an aliphatic isocyanate compound, an alicyclic isocyanate compound, and polyisocyanate derivatives thereof, may be mentioned.

The aromatic isocyanate compound may, for example, be tolylene diisocyanate (2,4- or 2,6-tolylene diisocyanate or a mixture thereof) (TDI), phenylene diisocyanate (m- or p-phenylene diisocyanate, or a mixture thereof), 4,4'-diphenyl diisocyanate, diphenylmethane diisocyanate (4,4'-, 2,4'- or 2,2'-diphenylmethane diisocyanate, or a mixtures thereof) (MDI), 4,4'-toluidine diisocyanate (TODI), 4,4'-diphenyl ether diisocyanate, xylylene diisocyanate (1,3- or 1,4-xylylene diisocyanate, or a mixture thereof) (XDI), tetramethylxylylene diisocyanate (1,3- or 1,4-tetramethylxylylene diisocyanate or a mixture thereof) (TMXDI), ω,ω'-diisocyanate-1,4-diethylbenzene, naphthalene diisocyanate (1,5-, 1,4- or 1,8-naphthalene diisocyanate or a mixture thereof) (NDI), triphenylmethane triisocyanate, tris(isocyanatephenyl) thiophosphate, polymethylene polyphenylene polyisocyanate, nitrodiphenyl-4,4'-diisocyanate, 3,3'-dimethyldiphenylmethane-4,4'-diisocyanate, 4,4'-diphenylpropane diisocyanate, 3,3'-dimethoxydiphenyl-4,4'-diisocyanate, etc.

The aliphatic isocyanate compound may, for example, be trimethylene diisocyanate, 1,2-propylene diisocyanate, butylene diisocyanate (tetramethylene diisocyanate, 1,2-butylene diisocyanate, 2,3-butylene diisocyanate, or 1,3-butylene diisocyanate), hexamethylene diisocyanate, pentamethylene diisocyanate, 2,2,4-trimethylhexamethylene diisocyanate, 2,4,4-trimethylhexamethylene diisocyanate, 2,6-diisocyanate methylcapate, lysine diisocyanate, lysine ester triisocyanate, 1,6,11-undecane triisocyanate, 1,3,6-hexamethylene triisocyanate, trimethylhexamethylene diisocyanate, decamethylene diisocyanate., etc.

The alicyclic isocyanate compound may, for example, be a monocyclic alicyclic isocyanate compound such as 1,3-cyclopentane diisocyanate, 1,3-cyclopentene diisocyanate, cyclohexane diisocyanate (1,4-cyclohexane diisocyanate, or 1,3-cyclohexane diisocyanate), 3-isocyanate methyl-3,5,5-trimethylcyclohexyl isocyanate (isophorone diisocyanate, IPDI), methylene bis(cyclohexyl isocyanate (4,4'-, 2,4'- or 2,2'-methylene bis(cyclohexyl isocyanate, or a mixture thereof) (hydrogenated MDI), methylcyclohexanediisocyanate (methyl-2,4-cyclohexanediisocyanate, methyl-2,6-cyclohexanediisocyanate, bis(isocyanatemethyl)cyclohexane (1,3- or 1,4-bis(isocyanatemethyl)cyclohexane, or a mixture thereof) (hydrogenated XDI), dimer acid diisocyanate, transcyclohexane 1,4-diisocyanate, hydrogenated tolylene diisocyanate (hydrogenated TDI), or hydrogenated tetramethylxylylene diisocyanate (hydrogenated TMXDI); a cyclic alicyclic isocyanate compound such as norbornene diisocyanate, norbornane diisocyanate methyl, bicycloheptane triisocyanate, diisocyanatomethyl bicycloheptane, or di(diisocyanatomethyl)tricyclodecane; etc.

Further, the derivatives of these polyisocyanates may, for example, be multimers of the above isocyanate compounds (dimers, trimers, pentamers, heptamers, uretidinediones, ureytonimines, isocyanurate modified products, polycarbodiimides, etc.), a urethane modified product (for example, a urethane modified product obtained by modifying or reacting a part of the isocyanate groups in the isocyanate compound or the multimer with a monool or a polyol), a biuret modified product (for example, a biuret modified product produced by reacting the above isocyanate compound with water), an allophanate modified product (for example, an allophanate modified product produced by a reaction of the above isocyanate compound with a monool or polyol component), an urea modified product (for example, an urea modified product produced by a reaction of the above isocyanate compound with a diamine), an oxadiazinetrione (for example, an oxadiazinetrione produced by a reaction of the above isocyanate compound with carbon dioxide gas), etc.

Here, as the above isocyanate compound or its derivative, one type may be used alone, or two or more types may be used in combination.

The polyurethane-forming composition may contain various additives. With the polyurethane-forming composition containing additives, the effects of the additives are expected.

As the additives, a catalyst, a foam stabilizer, a cross-linking agent, a communicating agent, a foaming agent, a dye, an organic pigment, an inorganic pigment, an inorganic reinforcing material, a plasticizer, a processing aid, an ultraviolet absorber, a light stabilizer, a lubricant, a wax, a crystal nucleating agent, a release agent, a hydrolysis inhibitor, an antifogging agent, a dustproofing agent, a rustproofing agent, an ion trap agent, a flame retardant, a flame retardant aid, an inorganic filler, an organic filler, etc. may be mentioned.

EXAMPLES

In the following, the respective embodiments of the present invention will be described with reference to Examples, but these Examples do not limit the respective embodiments of the present invention. First, the evaluation/measurement methods used in Examples and Comparative Examples will be shown.

(1) NMR of Phosphazenium Salt $^1$H-NMR was measured using a nuclear magnetic resonance (NMR) spectrum measuring device (manufactured by JEOL Ltd., (trade name) GSX270WB) using deuterated chloroform as a heavy solvent.

(2) pH of Phosphazenium Salt

A 0.01 mol/L phosphazenium salt aqueous solution was attached to a pH test paper, and the pH of the phosphazenium salt was measured.

(3) pH of Polyalkylene Oxide

In accordance with the method described in JIS K-1557-5, 10 g of a polyalkylene oxide was dissolved in a mixed solvent (60 mL) of isopropanol/water=10/6, and using a pH/ORP meter PH72 manufactured by YOKOGAWA, the pH of the polyalkylene oxide was measured.

(4) Amounts of Aldehydes Votatilized from Polyalkylene Oxide 10 g of a polyalkylene oxide was put in an impinger (manufactured by Suenaga Rikagaku Co., Ltd., capacity: 30 ml), and while heating at 65° C. for 2 hours, nitrogen gas aerated with a hydrocarbon trap was blown in at 65° C. at a flow rate of 0.5 L/min. The gas after aeration was collected in a 2,4-dinitrophenylhydrazine (DNPH) cartridge, and using 5 ml of an eluent, the adsorbed component was eluted. The eluate was measured by high performance liquid chromatography (HPLC) to measure the amounts of aldehydes volatilized from the polyalkylene oxide.

(5) Hydroxyl Value of Polyalkylene Oxide (Unit: mgKOH/g)

Calculated by the method described in JIS K-1557-1.

(6) Odor of Polyalkylene Oxide Composition 10 g of a polyalkylene oxide composition was put in a 20 ml sample tube, left for 12 hours in a sealed state, and then opened to evaluate the presence or absence of odor.

(7) Turbidity of Polyalkylene Oxide 10 g of a polyalkylene oxide composition was put in a 20 ml sample tube and visually observed, whereby the presence or absence of turbidity was evaluated.

(8) Odor of Polyurethane-Forming Composition

A polyurethane-forming composition immediately after the production was put in a sample bottle and left to stand still for 1 hour in a sealed state. At the time when opened, the presence or absence of odor was evaluated.

Synthesis Example 1

A 2 L four-necked flask equipped with a stirring blade was made to be under a nitrogen atmosphere, and 96 g (0.46 mol) of phosphorus pentachloride and 800 ml of dehydrated toluene were added and stirred at 20° C. While maintaining stirring, 345 g (2.99 mol) of 1,1,3,3-tetramethylguanidine was added dropwise over 3 hours, then the temperature was raised to 100° C., and further 107 g (0.92 mol) of 1,1,3,3-tetramethylguanidine was added dropwise over 1 hour. The obtained white slurry solution was stirred at 100° C. for 14 hours and then cooled to 80° C., and 250 ml of ion-exchanged water was added and further stirred for 30 minutes. When the stirring was stopped, the slurry had been completely dissolved, and a two-phase solution was obtained. The obtained two-phase solution was separated into oil and water, and the aqueous phase was recovered. To the obtained aqueous phase, 100 ml of dichloromethane was added to conduct oil-water separation, whereupon the dichloromethane phase was recovered. The obtained dichloromethane solution was washed with 100 ml of deionized water.

The obtained dichloromethane solution was transferred to a 2 L four-necked flask equipped with a stirring blade, 900 g of 2-propanol was added, and then the temperature was raised to 80 to 100° C. under normal pressure to remove dichloromethane. The obtained 2-propanol solution was allowed to cool to an internal temperature of 60° C. with stirring, and then, 31 g (0.47 mol) of 85 mass % potassium hydroxide was added and reacted at 60° C. for 2 hours. The temperature was cooled to 25° C., and the precipitated by-product salt was removed by filtration to obtain 860 g of a 2-propanol solution of monovalent phosphazenium salt-A at a concentration of 25 mass % in a yield of 92%. The phosphazenium salt-A is a phosphazenium salt corresponding to the above formula (5) in which $R^1$ is a methyl group, $R^2$ is a methyl group, and $X^-$ is a hydroxy anion. The pH of the obtained phosphazenium salt-A was 12 (basic).

Then, $^1$H-NMR of the obtained phosphazenium salt-A was measured.

FIG. 1 is a diagram showing $^1$H-NMR of the phosphazenium salt-A obtained in Synthesis Example 1.

1.21 (d, 72H, methyl group of 2-propanol), 2.83 (s, 48H, methyl group of monovalent phosphazenium salt), 4.02 (sep, 12H, methine of 2-propanol).

Further, the phosphazenium salt-A was subjected to heat treatment at 120° C. for 8 hours, and as a result, a strong odor was generated, and formation of an impurity peak was confirmed by $^1$H-NMR.

Synthesis Example 2

A 100 ml Schlenk tube equipped with a magnetic rotor was made to be under a nitrogen atmosphere, and 5.7 g of tetrakis[tris(dimethylamino)phosphoranylideneamino]phosphonium chloride (7.4 mmol, manufactured by Sigma-Aldrich) and 16 ml of 2-propanol were added and dissolved by stirring at 25° C. While maintaining stirring, a solution in which 0.53 g of 85 wt % potassium hydroxide (8.1 mmol, 1.1 mol equivalent to tetrakis[tris(dimethylamino)phosphoranylideneamino]phosphonium chloride) was dissolved in 2-propanol, was added. After stirring at 25° C. for 5 hours, the precipitated by-product salt was removed by filtration to obtain 33 g of a 2-propanol solution of monovalent phosphazenium salt-A' at a concentration of 17 mass % in a yield of 98%. The phosphazenium salt-A' is a phosphazenium salt corresponding to the above formula (6) in which $R^1$ is a methyl group, $R^2$ is a methyl group and $X^-$ is a hydroxy anion. The pH of the obtained phosphazenium salt-A' was 12 (basic).

Then, $^1$H-NMR of the obtained phosphazenium salt-A' was measured. The chemical shift of the monovalent phosphazenium cation in $^1$H-NMR was 2.62 ppm.

Further, the phosphazenium salt-A' was subjected to a heat treatment at 120° C. for 8 hours, and as a result, a strong odor was generated, and formation of an impurity peak was confirmed by $^1$H-NMR.

Test Example 1

To a 100 ml beaker containing a stirrer bar, 10 mg of the 2-propanol solution of monovalent phosphazenium salt-A obtained in Synthesis Example 1 and 60 ml of a mixed solution of isopropanol/water=10/6 were added and thoroughly stirred. By dropwise adding an isopropanol solution of dodecylbenzenesulfonic acid (0.02 mol/L) thereto, neutralization titration was carried out. The results are shown in FIG. 2.

Figure 2:
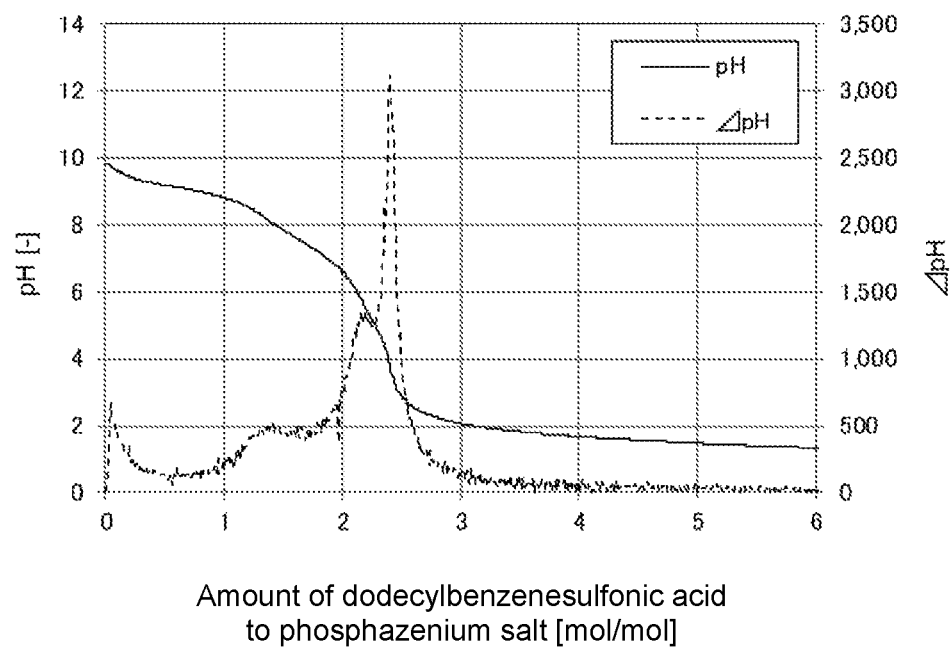
FIG. 2 is a diagram showing a change in pH during neutralization titration of the phosphazenium salt-A obtained in Synthesis Example 1.

FIG. 2 is a diagram showing a change in pH in the neutralization titration of the phosphazenium salt-A obtained in Synthesis Example 1. In FIG. 2, the vertical axis represents the pH or the amount of change in pH, and the horizontal axis represents the ratio (mol/mol) of the number of moles of dodecylbenzenesulfonic acid to the number of moles of phosphazenium salt-A.

According to FIG. 2, an equivalence point was observed at the time when about 2 mol of dodecylbenzenesulfonic acid was dropwise added to 1 mol of monovalent phosphazenium salt-A, and formation of a divalent phosphazenium salt was confirmed. The divalent phosphazenium salt is a phosphazenium salt corresponding to the above formula (2) in which $R^1$ is a methyl group, $R^2$ is a methyl group and $A^-$ is a deprotonated form of dodecylbenzenesulfonic acid.

Test Example 2

To a 100 ml beaker containing a stirrer bar, 95 mg of the 2-propanol solution of monovalent phosphazenium salt-A' obtained in Synthesis Example 2 and 60 ml of methanol were added and thoroughly stirred. By dropwise adding an isopropanol solution of dodecylbenzenesulfonic acid (0.02 mol/L) thereto, neutralization titration was carried out.

An equivalence point was observed at the time when about 2 mol of dodecylbenzenesulfonic acid was dropwise added to 1 mol of monovalent phosphazenium salt-A', and formation of a divalent phosphazenium salt was confirmed. The divalent phosphazenium salt is a phosphazenium salt corresponding to the above formula (3) in which $R^1$ is a methyl group, $R^2$ is a methyl group and $[A^{n-}]_m$ is a deprotonated form of dodecylbenzenesulfonic acid.

Example 1

A 0.2 L four-necked flask containing a stirrer bar was made to be under a nitrogen atmosphere, and 50 g (36 mmol) of a 2-propanol solution of monovalent phosphazenium salt-A obtained in Synthesis Example 1 was added. While maintaining stirring, 22 g of dodecylbenzenesulfonic acid (72 mmol, 2 mol per 1 mol of monovalent phosphazenium salt) was added thereto. By continuing stirring for 10 minutes, the target divalent phosphazenium salt-B was obtained. The divalent phosphazenium salt-B is a phosphazenium salt corresponding to the above formula (2) in which $R^1$ is a methyl group, $R^2$ is a methyl group and $A^-$ is a deprotonated form of dodecylbenzenesulfonic acid. The pH of the obtained phosphazenium salt was 7 (neutral).

Then, $^1$H-NMR of the obtained phosphazenium salt-B was measured.

Figure 3:
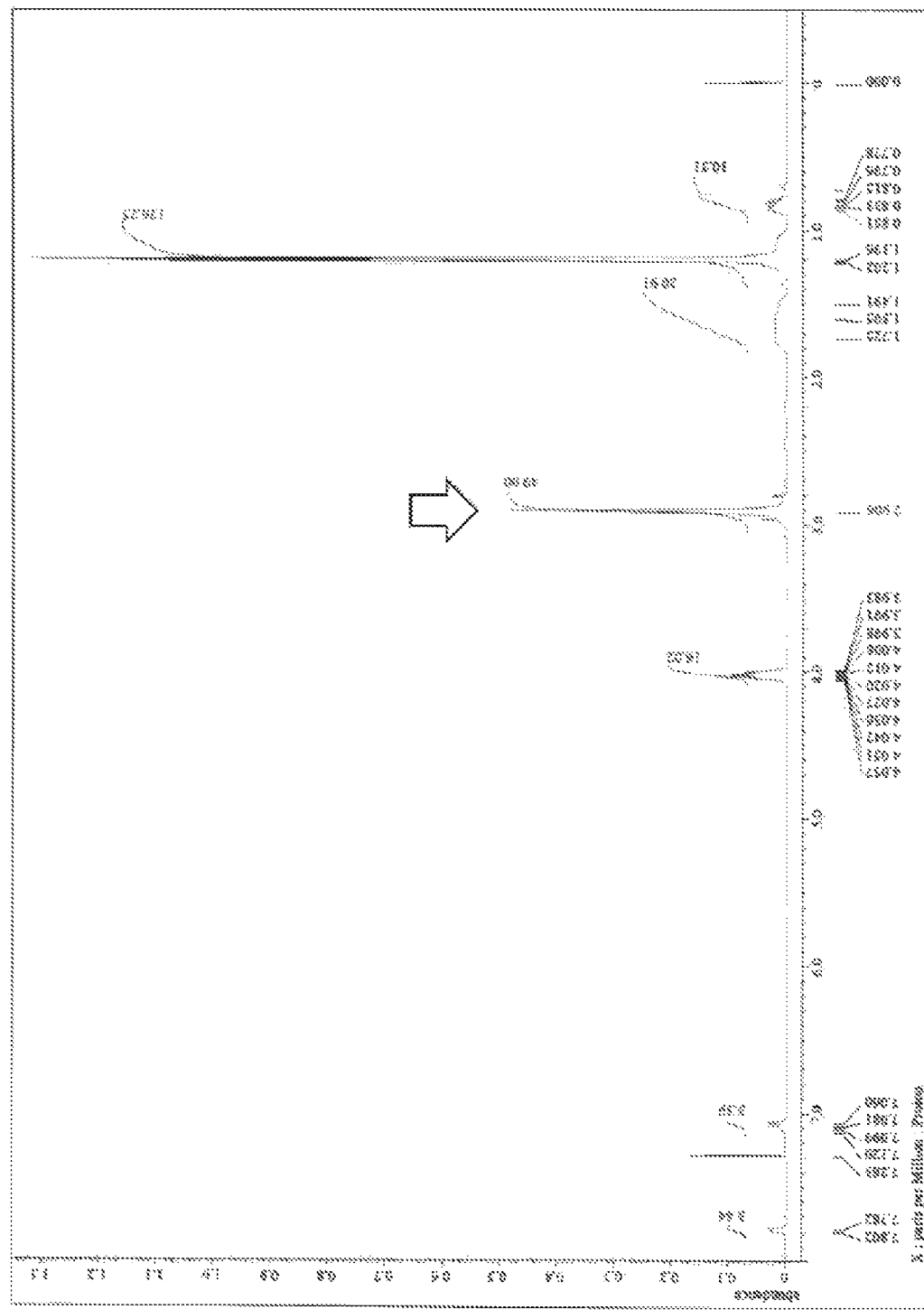
FIG. 3 is a diagram showing ¹H-NMR of a phosphazenium salt-B obtained in Example 1.

FIG. 3 is a diagram showing $^1$H-NMR of the phosphazenium salt-B obtained in Example 1.

1.20 (d, 96H, methyl group of 2-propanol), 0.70 to 1.80 (m, 50H, alkyl group of dodecylbenzenesulfonic acid), 2.91 (s, 49H, methyl group and additional proton of divalent phosphazenium salt), 4.02 (sep, 16H, methine of 2-propanol), 7.07 (d, 4H, phenyl group of dodecylbenzenesulfonic acid), 7.79 (d, 4H, phenyl group of dodecylbenzenesulfonic acid). The chemical shift of the divalent phosphazenium cation in $^1$H-NMR was 2.91 ppm, which was shifted to a lower magnetic field as compared with the monovalent phosphazenium salt-B obtained in Synthesis Example 1. The present inventors presume that by the change of the valence of the phosphazenium salt from monovalent to divalent, the cationicity of the phosphazenium salt was increased (the electron density was decreased).

Further, the phosphazenium salt-B was subjected to heat treatment at 120° C. for 8 hours, and as a result, no odor was confirmed, and no major change in $^1$H-NMR was confirmed, and it was stable.

17 mg of the obtained divalent phosphazenium salt-B was added to 10 g of polyalkylene oxide having a pH of 6.4 (neutral) and an acetaldehyde volatilization amount of 0.92 ppm, and thoroughly stirred. The obtained polyalkylene oxide remained neutral (pH: 7.3), and the acetaldehyde volatilization amount was reduced to 0.14 ppm. The present inventors presume that acetaldehyde was captured by the divalent phosphazenium salt and was less likely to volatilize.

Example 2

A 0.2 L four-necked flask containing a stirrer bar was made to be under a nitrogen atmosphere, and 50 g (11 mmol) of a 2-propanol solution of monovalent phosphazenium salt-A' obtained in Synthesis Example 2 was added. While maintaining stirring, 7.5 g of dodecylbenzenesulfonic acid (23 mmol, 2.1 mol to 1 mol of monovalent phosphazenium salt) was added thereto. After continuing stirring for 10 minutes, the solvent was removed under reduced pressure to obtain the target divalent phosphazenium salt-B'. The divalent phosphazenium salt-B' is a phosphazenium salt corresponding to the above formula (3) in which $R^1$ is a methyl group, $R^2$ is a methyl group, and $[A^{n-}]_m$ is a deprotonated form of dodecylbenzenesulfonic acid. The pH of the obtained phosphazenium salt was 7 (neutral).

Then, $^1$H-NMR of the obtained phosphazenium salt-B' was measured. The chemical shift of the divalent phosphazenium cation in $^1$H-NMR was 2.70 ppm, which was shifted to a lower magnetic field as compared with the monovalent phosphazenium salt-A' obtained in Synthesis Example 2. The present inventors presume that by the change of the valence of the phosphazenium salt from monovalent to divalent, the cationicity of the phosphazenium salt was increased (electron density was decreased).

Further, the phosphazenium salt-B' was subjected to heat treatment at 120° C. for 8 hours, and as a result, no odor was confirmed, and no major change in $^1$H-NMR was confirmed, and it was stable.

31 mg of the obtained divalent phosphazenium salt-B' was added to 10 g of polyalkylene oxide having a pH of 6.4 (neutral) and an acetaldehyde volatilization amount of 0.92 ppm, and thoroughly stirred. While the obtained polyalkylene oxide was kept neutral (pH: 7.4), the acetaldehyde volatilization amount was reduced to 0.53 ppm. The present inventors presume that acetaldehyde was captured by the divalent phosphazenium salt and was less likely to volatilize.

Comparative Example 1

A 0.2 L four-necked flask containing a stirrer bar was made to be under a nitrogen atmosphere, and 50 g (36 mmol) of a 2-propanol solution of monovalent phosphazenium salt-A obtained in Synthesis Example 1 was added. While maintaining stirring, 11 g of dodecylbenzenesulfonic acid (36 mmol, 1 mol to 1 mol of monovalent phosphazenium salt) was added thereto. By continuing stirring for 10 minutes, the target monovalent phosphazenium salt-C was obtained. The monovalent phosphazenium salt-C is a phosphazenium salt corresponding to the above formula (5) in which $R^1$ is a methyl group, $R^2$ is a methyl group and $X^-$ is a deprotonated form of dodecylbenzenesulfonic acid. The pH of the obtained phosphazenium salt-C was 12, which was strongly basic.

Then, $^1$H-NMR of the obtained phosphazenium salt-C was measured.

Figure 4:
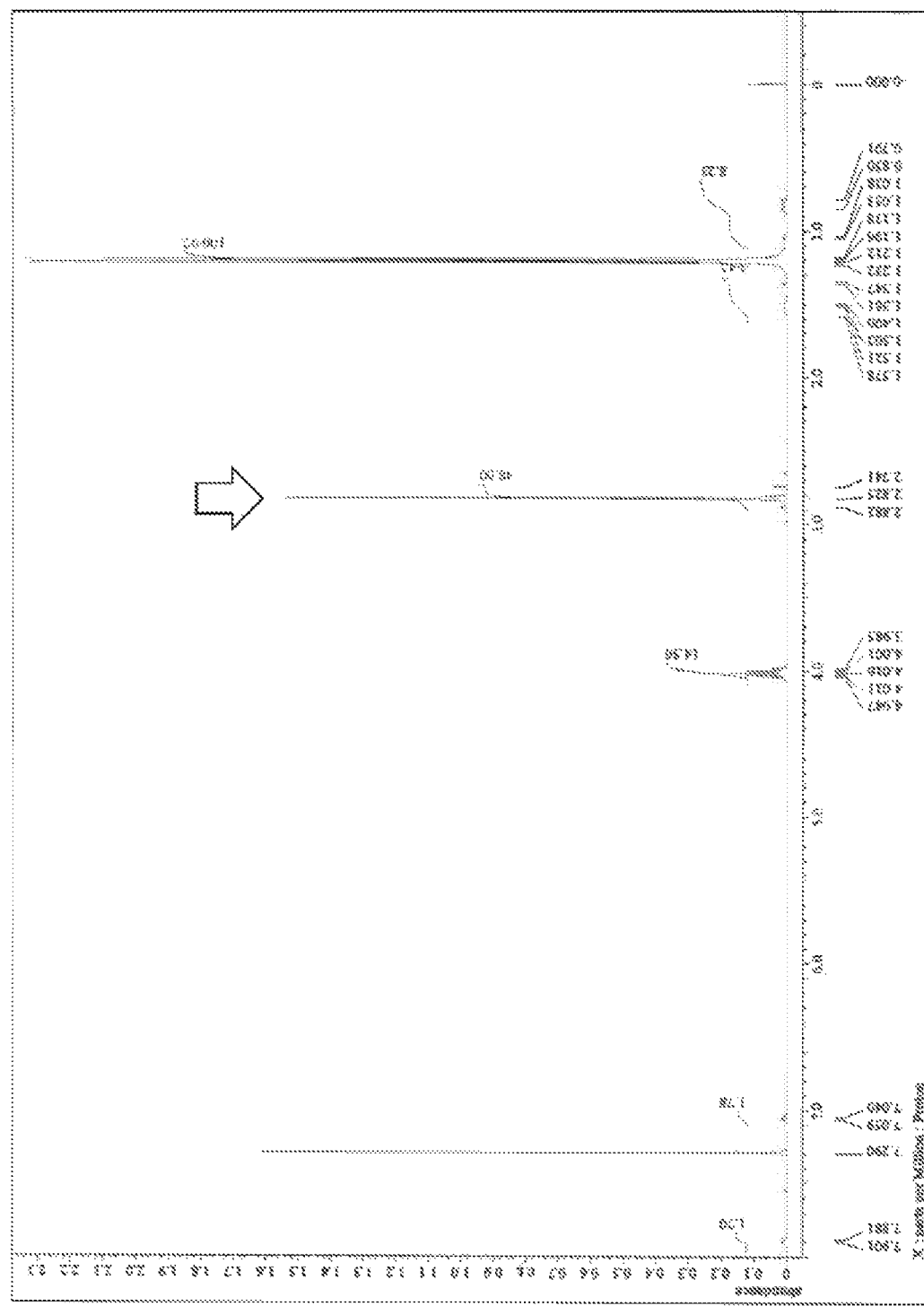
FIG. 4 is a diagram showing ¹H-NMR of a phosphazenium salt-C obtained in Comparative Example 1.

FIG. 4 is a diagram showing $^1$H-NMR of the phosphazenium salt-C obtained in Comparative Example 1.

1.20 (d, 90H, methyl group of 2-propanol), 0.70 to 1.70 (m, 25H, alkyl group of dodecylbenzenesulfonic acid), 2.83 (s, 48H, methyl group of monovalent phosphazenium salt)), 4.02 (sep, 15H, methine of 2-propanol), 7.05 (d, 2H, phenyl group of dodecylbenzenesulfonic acid), 7.89 (d, 2H, phenyl group of dodecylbenzenesulfonic acid).

The chemical shift of the monovalent phosphazenium cation in $^1$H-NMR was 2.83 ppm, which was a high magnetic field as compared with the divalent phosphazenium salt-B obtained in Example 1 (FIG. 4). The present inventors presume that the cationicity was decreased (electron density was increased) as compared with the divalent phosphazenium salt-B.

42 mg of the obtained 2-propanol solution of monovalent phosphazenium salt-C was added to 10 g of polyalkylene oxide having a pH of 6.4 (neutral) and an acetaldehyde volatilization amount of 0.92 ppm, and thoroughly stirred. The obtained polyalkylene oxide had a pH of 10.6 and thus showed a strong basicity. The amount of acetaldehyde volatilized from the obtained polyalkylene oxide was 0.94 ppm, and no aldehyde scavenging effect was observed.

Comparative Example 2

A 0.2 L four-necked flask containing a stirrer bar was made to be under a nitrogen atmosphere, and 50 g (11 mmol) of a 2-propanol solution of monovalent phosphazenium salt-A' obtained in Synthesis Example 2 was added. While maintaining stirring, 3.6 g of dodecylbenzenesulfonic acid (11 mmol, 1 mol to 1 mol of monovalent phosphazenium salt) was added thereto. After continuing stirring for 10 minutes, the solvent was removed under reduced pressure to obtain the desired monovalent phosphazenium salt-C'. The monovalent phosphazenium salt-C' is a phosphazenium salt corresponding to the above formula (6) in which $R^1$ is a methyl group, $R^2$ is a methyl group and $X^-$ is a deprotonated form of dodecylbenzenesulfonic acid. The obtained phosphazenium salt-C' had a pH of 12 and thus showed a strong basicity.

Then, $^1$H-NMR of the obtained phosphazenium salt-C' was measured. The chemical shift of the monovalent phosphazenium cation in $^1$H-NMR was 2.62 ppm, which was a high magnetic field as compared with the divalent phosphazenium salt-B' obtained in Example 2. The present inventors presume that the cationicity was decreased (the electron density was increased) as compared with the divalent phosphazenium salt-B'.

22 mg of the obtained monovalent phosphazenium salt-C' was added to 10 g of polyalkylene oxide having a pH of 6.4 (neutral) and an acetaldehyde volatilization amount of 0.92 ppm, and thoroughly stirred. The obtained polyalkylene oxide had a pH of 8.6 and thus was basic. The amount of acetaldehyde volatilized from the obtained polyalkylene oxide was 0.96 ppm, and no aldehyde scavenging effect was observed.

Example 3

A 0.2 L four-necked flask containing a stirrer bar was made to be under a nitrogen atmosphere, and 50 g (36 mmol) of a 2-propanol solution of monovalent phosphazenium salt-A obtained in Synthesis Example 1 was added. While maintaining stirring, 23 g of dodecylbenzenesulfonic acid (76 mmol, 2.1 mol to 1 mol of monovalent phosphazenium salt) was added thereto. By continuing stirring for 10 minutes, a divalent phosphazenium salt (a phosphazenium salt corresponding to the above formula (2) in which $R^1$ is a methyl group, $R^2$ is a methyl group and $A^-$ is a deprotonated form of dodecylbenzenesulfonic acid) was obtained.

To a 2 L four-necked flask equipped with a stirring blade, 1,200 g of a polypropylene oxide having a molecular weight of 7,000 and 2.8 g of the obtained divalent phosphazenium salt were added and stirred at an internal temperature of 80° C. for 1 hour to obtain 1,203 g of a polyalkylene oxide composition containing 2,300 ppm of the divalent phosphazenium salt. The obtained polyalkylene oxide composition was odorless, had no turbidity, had a pH of 7.2, a hydroxy value of 24 mgKOH/g, an acetaldehyde volatilization amount of 0.40 ppm, and a propionaldehyde volatilization amount of 0.04 ppm.

The obtained polyalkylene oxide composition and MDI were mixed so that the molar ratio of the isocyanate group (NCO) in MDI to the hydroxy group (OH) in the polyalkylene oxide composition became 1.5, and reacted until the NCO group was completely consumed, to synthesize a polyurethane-forming composition. The obtained polyurethane-forming composition was odorless.

Example 4

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1, were added, and, under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then unreacted propylene oxide was removed under a reduced pressure of 0.5 kPa. Further, while maintaining an internal temperature of 130° C. and a pressure of at most 0.3 MPa, 173 g of ethylene oxide was intermittently supplied to carry out a polymerization reaction of ethylene oxide, and then unreacted ethylene oxide was removed under a reduced pressure of 0.5 kPa. Thereafter, at an internal temperature of 80° C., 2.0 g of dodecylbenzenesulfonic acid (6.25 mmol, 2.5 mol to 1 mol of monovalent phosphazenium salt) and Irganox 1135 (0.91 g) were added and stirred for 1 hour to obtain 1,210 g of a polyalkylene oxide composition containing a divalent phosphazenium salt (a phosphazenium salt corresponding to the above formula (2) in which $R^1$ is a methyl group, $R^2$ is a methyl group and $A^-$ is a deprotonated form of dodecylbenzenesulfonic acid). The obtained polyalkylene oxide composition was odorless, had no turbidity, had a pH of 6.5, had a hydroxy value of 24 mgKOH/g, had an acetaldehyde volatilization amount of 0.14 ppm, and had a propionaldehyde volatilization amount of 0.12 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition was odorless.

Example 5

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1, was added, and, under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then, under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then, under a reduced pressure of 0.5 kPa, unreacted ethylene oxide was removed. Then, at an internal temperature of 80° C., 2.4 g of dodecylbenzenesulfonic acid (7.5 mmol, 3 mol to 1 mol of monovalent phosphazenium salt) and Irganox 1135 (0.91 g) were added and stirred for 1 hour to obtain 1,210 g of a polyalkylene oxide composition containing a divalent phosphazenium salt (a phosphazenium salt corresponding to the above formula (2) in which $R^1$ is a methyl group, $R^2$ is a methyl group and $A^-$ is a deprotonated form of dodecylbenzenesulfonic acid). The obtained polyalkylene oxide composition was odorless, had no turbidity, had a pH of 5.6, had a hydroxy value of 24 mgKOH/g, had an acetaldehyde volatilization amount of 0.24 ppm, and had a propionaldehyde volatilization amount of 0.24 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition was odorless.

Example 6

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1, were added, and at an internal temperature of 80° C. and under a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then under a reduced pressure of 0.5 kPa, unreacted ethylene oxide was removed. Then, at an internal temperature of 80° C., 0.86 g of p-toluenesulfonic acid (5.0 mmol, 2 mol to 1 mol of monovalent phosphazenium salt) and Irganox 1135 (0.91 g) were added and stirred for 1 hour to obtain 1,200 g of a polyalkylene oxide composition containing a divalent phosphazenium salt (a phosphazenium salt corresponding to the above formula (2) wherein $R^1$ is a methyl group, $R^2$ is a methyl group and $A^-$ is a deprotonated form of p-toluenesulfonic acid). The obtained polyalkylene oxide composition was odorless, had no turbidity, had a pH of 7.3, a hydroxy value of 24 mgKOH/g and had an aldehyde volatilization amount of 0.3 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition was odorless.

Example 7

In a 0.2 L four-necked flask containing a stirrer bar was made to be under a nitrogen atmosphere, and 50 g (11 mmol) of a 17 mass % 2-propanol solution of monovalent phosphazenium salt-A' obtained in Synthesis Example 2, was added. While maintaining stirring, 7.5 g of dodecylbenzenesulfonic acid (23 mmol, 2.1 mol to 1 mol of monovalent phosphazenium salt) was added thereto. After continuing stirring for 10 minutes, the solvent was removed under reduced pressure to obtain a divalent phosphazenium salt (a phosphazenium salt corresponding to the above formula (3) in which $R^1$ is a methyl group, $R^2$ is a methyl group and $[A^{n-}]_m$ is a deprotonated form of dodecylbenzenesulfonic acid).

In a 2 L four-necked flask equipped with a stirring blade, 1,200 g of polypropylene oxide with acetaldehyde volatilization amount: 0.92 ppm, propionaldehyde volatilization amount: 3.1 ppm, pH: 6.4 (neutral), and hydroxy value of 24 mg KOH/g and 3.7 g of the obtained divalent phosphazenium salt were added, and stirred at an internal temperature of 80° C. for 1 hour to obtain 1,204 g of a polyalkylene oxide composition containing 3,100 ppm of a divalent phosphazenium salt (a phosphazenium salt corresponding to the above formula (3) in which $R^1$ is a methyl group, $R^2$ is a methyl group and $[A^{n-}]_m$ is a deprotonated form of dodecylbenzenesulfonic acid). The obtained polyalkylene oxide composition was odorless, had no turbidity, had a pH of 7.4 (neutral), and had a hydroxy value of 24 mgKOH/g. The acetaldehyde volatilization amount was reduced to 0.53 ppm and the propionaldehyde volatilization amount was reduced to 0.11 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition was odorless.

Comparative Example 3

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1, were added, and under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then under a reduced pressure of 0.5 kPa, unreacted ethylene oxide was removed. Then, at an internal temperature of 85° C., 30 g of water and 12 g of KYOWARD 700SEN-S (adsorbent manufactured by Kyowa Chemical Industry Co., Ltd.) were added and stirred for 1 hour. Further, the temperature was raised to 120° C., the mixture was stirred for 3 hours, dehydration treatment was carried out for 3 hours under a reduced pressure of 0.5 kPa, and then the adsorbent was removed by filtration to obtain 1,210 g of a polyalkylene oxide composition containing no divalent phosphazenium salt. The obtained polyalkylene oxide composition was odorless, had no turbidity, had a pH of 6.8, had a hydroxy value of 24 mgKOH/g, had a high acetaldehyde volatilization amount of 0.92 ppm, and had a high propionaldehyde volatilization amount of 3.1 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition had a slight odor.

Comparative Example 4

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1 were added, and under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then under a reduced pressure of 0.5 kPa, unreacted ethylene oxide was removed. Then, at an internal temperature of 80° C., 0.8 g of dodecylbenzenesulfonic acid (2.5 mmol, 1.0 mol to 1 mol of monovalent phosphazenium salt) and Irganox 1135 (0.91 g) were added, and stirred for 1 hour to obtain 1,210 g of a polyalkylene oxide composition containing a monovalent phosphazenium salt (a phosphazenium salt corresponding to the above formula (5) in which $R^1$ is a methyl group, $R^2$ is a methyl group and $X^-$ is a deprotonated form of dodecylbenzenesulfonic acid). The obtained polyalkylene oxide composition had an odor, was not cloudy, had a pH of 8.4, and showed basicity.

The obtained polyalkylene oxide composition and MDI were mixed so that the molar ratio of the isocyanate group (NCO) in MDI to the hydroxy group (OH) in the polyalkylene oxide composition became to be 1.5, but because the composition was basic, it was not possible to obtain a polyurethane forming composition.

Comparative Example 5

In a 2 L autoclave equipped with a stirring blade, 100 g of polypropylene triol having a molecular weight of 600 and 5.1 g of a 25 mass % 2-propanol solution of 1.3 g (2.5 mmol) of monovalent phosphazenium salt-A obtained in Synthesis Example 1 were added, and under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then under a reduced pressure of 0.5 kPa, unreacted ethylene oxide was removed. Then, at an internal temperature of 80° C., 5.0 mL of a 1.0 mol/L hydrochloric acid aqueous solution (5.0 mmol, 2 mol to 1 mol of monovalent phosphazenium salt) and Irganox 1135 (0.91 g) were added, and under reduced pressure, water was removed, to obtain 1,210 g of a polyalkylene oxide composition containing a divalent phosphazenium salt (a phosphazenium salt corresponding to the above formula (2) in which $R^1$ is a methyl group, $R^2$ is a methyl group and $A^-$ is a chlorine anion). The obtained polyalkylene oxide composition was odorless, was cloudy and had a pH of 7.2.

The obtained polyalkylene oxide composition and MDI were mixed so that the molar ratio of the isocyanate group (NCO) in MDI to the hydroxy group (OH) in the polyalkylene oxide composition became to be 1.5, to synthesize a polyurethane-forming composition. The obtained polyurethane-forming composition was cloudy due to the cloudiness of the polyalkylene oxide composition.

Comparative Example 6

In a 2 L autoclave equipped with a stirring blade, 100 g of polypropylene triol having a molecular weight of 600 and 11 g (2.5 mmol) of a 17 mass % 2-propanol solution of monovalent phosphazenium salt-A' obtained in Synthesis Example 2 were added, and under an internal temperature of 80° C. and a reduced pressure of 0.5 kPa, 2-propanol was removed. Subsequently, while maintaining an internal temperature of 90° C. and a pressure of at most 0.3 MPa, 946 g of propylene oxide was intermittently supplied to carry out a polymerization reaction of propylene oxide, and then under a reduced pressure of 0.5 kPa, unreacted propylene oxide was removed. Further, while maintaining an internal temperature of 130° C. and a pressure of at most 0.3 MPa, 173 g of ethylene oxide was intermittently supplied to carry out a polymerization reaction of ethylene oxide, and then under a reduced pressure of 0.5 kPa, unreacted ethylene oxide was removed. Then, at an internal temperature of 85° C., 30 g of water and 12 g of KYOWARD 700SEN-S (adsorbent manufactured by Kyowa Chemical Industry Co., Ltd.) were added and stirred for 1 hour. Further, the temperature was raised to 120° C., the mixture was stirred for 3 hours, dehydration treatment was carried out for 3 hours under a reduced pressure of 0.5 kPa, and then the adsorbent was removed by filtration to obtain 1,210 g a polyalkylene oxide composition containing no divalent phosphazenium salt. The obtained polyalkylene oxide composition was odorless, had no turbidity, had a pH of 6.9 (neutral), and had a hydroxy value of 24 mgKOH/g. Further, the obtained polyalkylene oxide composition had a high acetaldehyde volatilization amount of 0.95 ppm and a high propionaldehyde volatilization amount of 3.3 ppm.

The obtained polyalkylene oxide composition and MDI were mixed so that the molar ratio of the isocyanate group (NCO) in MDI to the hydroxy group (OH) in the polyalkylene oxide composition became to be 1.5, and reacted until the NCO group was completely consumed, to synthesize a polyurethane-forming composition. The obtained polyurethane-forming composition had a slight odor.

Comparative Example 7

A 0.2 L four-necked flask containing a stirrer bar was made to be under a nitrogen atmosphere, and 50 g (11 mmol) of a 17 mass % 2-propanol solution of monovalent phosphazenium salt-A' obtained in Synthesis Example 2, was added. While maintaining stirring, 3.6 g of dodecylbenzenesulfonic acid (11 mmol, 1.0 mol to 1 mol of monovalent phosphazenium salt) was added thereto. After continuing stirring for 10 minutes, the solvent was removed under reduced pressure to obtain a monovalent phosphazenium salt (cationic species was a tetrakis[tris(dimethylamino)phosphoranylideneamino]phosphonium cation, and anionic species was a protonated form of dedecylbenzenesulfonic acid).

In a 2 L four-necked flask equipped with a stirring blade, 1,200 g of polypropylene oxide with acetaldehyde volatilization amount: 0.92 ppm, propionaldehyde volatilization amount: 3.1 ppm, pH: 6.4 (neutral) and hydroxy value of 24 mg KOH/g, and 2.8 g of the obtained monovalent phosphazenium salt, were added and stirred at an internal temperature of 80° C. for 1 hour, to obtain 1,203 g of a polyalkylene oxide composition containing 2,300 ppm of a monovalent phosphazenium salt (cation species was tetrakis[tris(dimethylamino)phosphoranylideneamino]phosphonium cation and anion species was a deprotonated form of dodecylbenzenesulfonic acid). The obtained polyalkylene oxide composition had an odor, was not cloudy, had a pH of 8.6 and showed basicity.

The obtained polyalkylene oxide composition and MDI were mixed so that the molar ratio of the isocyanate group (NCO) in MDI to the hydroxy group (OH) in the polyalkylene oxide composition became to be 1.5, but because the composition was basic, it was not possible to obtain a polyurethane forming composition.

Comparative Example 8

A 0.2 L four-necked flask containing a stirrer bar was made to be under a nitrogen atmosphere, and 50 g (11 mmol) of a 17 mass % 2-propanol solution of monovalent phosphazenium salt-A' obtained in Synthesis Example 2, was added. While maintaining stirring, 23 mL of a 1.0 mol/L hydrochloric acid solution (23 mmol, 2.1 mol to 1 mol of monovalent phosphazenium salt) was added thereto. After continuing stirring for 10 minutes, the solvent was removed under reduced pressure to obtain a divalent phosphazenium salt (a phosphazenium salt corresponding to the above formula (3) in which $R^1$ is a methyl group, $R^2$ is a methyl group and $[A^{n-}]_m$ is a chlorine anion).

In a 2 L four-necked flask equipped with a stirring blade, 1,200 g of polypropylene oxide having a pH of 6.4 (neutral) and a hydroxy value of 24 mgKOH/g, and 2.1 g of the obtained divalent phosphazenium salt, were added and stirred at a temperature of 80° C. for 1 hour, to obtain 1,202 g of a polyalkylene oxide composition containing 2,300 ppm of a divalent phosphazenium salt (a phosphazenium salt corresponding to the above formula (3) in which $R^1$ is a methyl group, $R^2$ is a methyl group and $[A^{n-}]_m$ is a chlorine anion). The obtained polyalkylene oxide composition was odorless, was cloudy and had a pH of 7.1.

The obtained polyalkylene oxide composition and MDI were mixed so that the molar ratio of the isocyanate group (NCO) in MDI to the hydroxy group (OH) in the polyalkylene oxide composition became to be 1.5, to synthesize a polyurethane-forming composition. The obtained polyurethane-forming composition was cloudy due to the cloudiness of the polyalkylene oxide composition.

The divalent phosphazenium salt according to one embodiment of the present invention is neutral and is excellent in thermal stability and aldehyde scavenging effect. Therefore, for example, by adding the divalent phosphazenium salt to a polyalkylene oxide, it is possible to obtain a polyalkylene oxide having a small amount of aldehyde volatilization. Such a polyalkylene oxide can be expected to be applied to polyurethanes, polyesters, surfactants, lubricants, etc.

Further, the polyalkylene oxide composition according to one embodiment of the present invention is odorless, has no turbidity and has a small amount of aldehyde volatilization, and thus is useful as a polyurethane raw material, a polyester raw material, a surfactant raw material, a lubricant raw material, etc. In particular, by reacting with various isocyanate compounds, it is expected to be developed into rigid foams to be used for heat insulation materials, into soft foams to be used for automobile seats, cushions, bedding, etc. and into adhesives, paints, sealing materials, thermosetting elastomers and thermoplastic elastomers.

In the foregoing, the present invention has been described in detail and with reference to specific embodiments, but it is apparent to those skilled in the art that various changes and modifications can be made without departing from the spirit and scope of the invention.

The entire disclosures of Japanese Patent Application No. 2018-041179 and Japanese Patent Application No. 2018-041180 filed on Mar. 7, 2018, Japanese Patent Application No. 2018-053366 filed on Mar. 20, 2018 and Japanese Patent Application No. 2018-057788 and Japanese Patent Application No. 2018-057789 filed on Mar. 26, 2018 including specifications, claims, drawings and summaries are incorporated herein by reference in their entireties.

The invention claimed is:

1. A divalent phosphazenium salt represented by the formula (1):

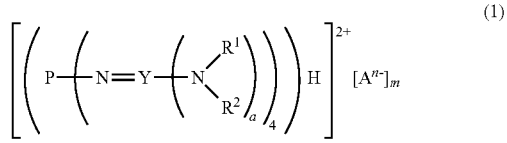

in the formula (1),
R$^1$ and R$^2$ represent each independently a hydrogen atom, a C$_{1-20}$ hydrocarbon group, a ring structure in which R$^1$ and R$^2$ are bonded to each other, or a ring structure in which a plurality of R$^1$ or R$^2$ are bonded to each other;
A$^{n-}$ represents a deprotonated form of an organic sulfonic acid or organic disulfonic acid;
either one of n and m is 1, and the other is 2; and
a is 2 when Y is a carbon atom and 3 when Y is a phosphorus atom.

2. A divalent phosphazenium salt represented by the formula (2):

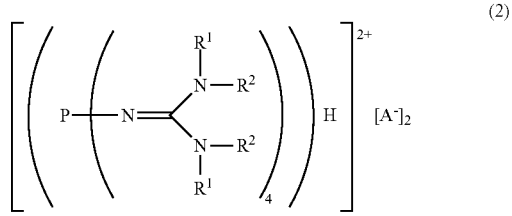

in the formula (2),
R$^1$ and R$^2$ represent each independently a hydrogen atom, a C$_{1-20}$ hydrocarbon group, a ring structure in which R$^1$ and R$^2$ are bonded to each other, or a ring structure in which a plurality of R$^1$ or R$^2$ are bonded to each other; and
A$^-$ represents a deprotonated form of an organic sulfonic acid.

3. A divalent phosphazenium salt represented by the formula (3):

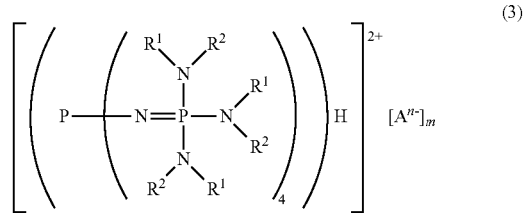

in the formula (3),
R$^1$ and R$^2$ represent each independently a hydrogen atom, a C$_{1-20}$ hydrocarbon group, or a ring structure in which R$^1$ and R$^2$ are bonded to each other;
A$^{n-}$ represents a deprotonated form of an organic sulfonic acid or organic disulfonic acid;
and
either one of n and m is 1, and the other is 2.

4. The divalent phosphazenium salt according to claim 1, characterized in that R$^1$ and R$^2$ are methyl groups, and A$^{n-}$ or A$^-$ is a deprotonated form of dodecylbenzenesulfonic acid, a linear alkylbenzenesulfonic acid (soft type), or a branched chain alkylbenzenesulfonic acid (hard type).

5. The divalent phosphazenium salt according to claim 1, characterized in that the pH of a 0.01 mol/L aqueous solution of the divalent phosphazenium salt is at least 5 and at most 8.

6. An aldehyde scavenger containing the divalent phosphazenium salt as defined in claim 1.

7. A method for producing the divalent phosphazenium salt as defined in claim 1, characterized by reacting at least 2 mol of an organic sulfonic acid to 1 mol of the phosphazenium salt represented by the formula (4):

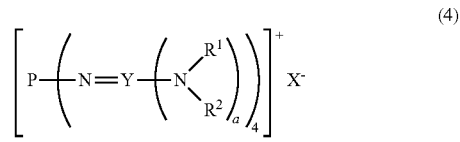

in the formula (4),
R$^1$ and R$^2$ represent each independently a hydrogen atom, a C$_{1-20}$ hydrocarbon group, a ring structure in which R$^1$ and R$^2$ are bonded to each other, or a ring structure in which a plurality of R$^1$ or R$^2$ are bonded each other;
X$^-$ represents a hydroxy anion, a C$_{1-4}$ alkoxy anion, a carboxy anion, a C$_{2-5}$ alkylcarboxy anion, or a hydrogen carbonate anion; and
a is 2 when Y is a carbon atom and 3 when Y is a phosphorus atom.

8. A method for producing the divalent phosphazenium salt as defined in claim 2, characterized by reacting at least 2 mol of an organic sulfonic acid to 1 mol of the phosphazenium salt represented by the formula (5):

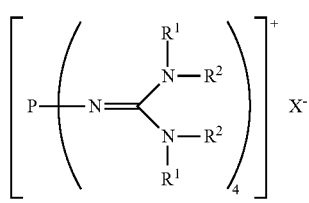
(5)

in the formula (5), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and $X^-$ is a hydroxy anion, a $C_{1-4}$ alkoxy anion, a carboxy anion, a $C_{2-5}$ alkylcarboxy anion, or a hydrogen carbonate anion.

9. The method for producing the divalent phosphazenium salt as defined in claim 3, characterized by reacting at least 2 mol of an organic sulfonic acid to 1 mol of the phosphazenium salt represented by the formula (6):

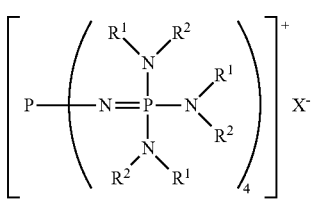
(6)

in the formula (6), $R^1$ and $R^2$ represent each independently a hydrogen atom, a $C_{1-20}$ hydrocarbon group, or a ring structure in which $R^1$ and $R^2$ are bonded to each other;

$X^-$ represents a hydroxy anion, a $C_{1-4}$ alkoxy anion, a carboxy anion, a $C_{2-5}$ alkylcarboxy anion, or a hydrogen carbonate anion.

10. A polyalkylene oxide composition characterized by comprising the divalent phosphazenium salt as defined in claim 1 and a polyalkylene oxide.

11. The polyalkylene oxide composition according to claim 10, characterized in that when measured by the following measurement method, the amount of volatilized acetaldehyde is at most 0.9 ppm, and the amount of volatilized propionaldehyde is at most 3.0 ppm:

[Measurement method]
(I): 10 g of the sample is put in a container having an internal volume of 30 ml,
(II): after (I), nitrogen bubbling is conducted at 0.5 L/min under heating at 65° C. for 2 hours to measure the amounts of volatilization.

12. The polyalkylene oxide composition according to claim 10, characterized in that the pH of the polyalkylene oxide composition measured in accordance with the method described in JIS K-1557-5 is at least 5 and at most 8.

13. A polyalkylene oxide composition characterized by comprising the divalent phosphazenium salt as defined in claim 2 and a polyalkylene oxide.

14. A polyurethane-forming composition comprising
(A) the polyalkylene oxide composition as defined in claim 10 and
(B) an isocyanate compound.

15. A method for producing the polyalkylene oxide composition as defined in claim 13, characterized in that a polymerization reaction of an alkylene oxide is conducted in the presence of the phosphazenium salt represented by the formula (5) and an active hydrogen-containing compound to produce a polyalkylene oxide, and then, at least 2 mol of an organic sulfonic acid is added to 1 mol of the phosphazenium salt:

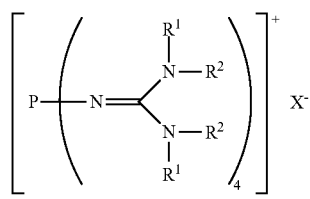
(5)

in the formula (5), $R^1$ and $R^2$ represent each independently a hydrogen atom, a $C_{1-20}$ hydrocarbon group, a ring structure in which $R^1$ and $R^2$ are bonded to each other, or a ring structure in which a plurality of $R^1$ or $R^2$ are bonded to each other; and $X^-$ represents a hydroxy anion, a $C_{1-4}$ alkoxy anion, a carboxy anion, a $C_{2-5}$ alkylcarboxy anion, or a hydrogen carbonate anion.

* * * * *